(12) United States Patent
McTavish

(10) Patent No.: US 12,642,948 B2
(45) Date of Patent: Jun. 2, 2026

(54) DERMAL PATCHES AND GLASS SWABS FOR APPLICATION OF TOPICAL IMMUNOSENSITIZERS

(71) Applicant: Squarex, LLC, Pine Springs, MN (US)

(72) Inventor: Hugh McTavish, Pine Springs, MN (US)

(73) Assignee: Squarex, LLC, Pine Springs, MN (US)

( * ) Notice: Subject to any disclaimer, the term of this patent is extended or adjusted under 35 U.S.C. 154(b) by 1177 days.

(21) Appl. No.: 17/463,170

(22) Filed: Aug. 31, 2021

(65) Prior Publication Data

US 2021/0393932 A1 Dec. 23, 2021

Related U.S. Application Data

(63) Continuation-in-part of application No. 16/932,111, filed on Jul. 17, 2020, now abandoned.

(60) Provisional application No. 63/040,138, filed on Jun. 17, 2020.

(51) Int. Cl.
| | |
|---|---|
| *A61M 35/00* | (2006.01) |
| *A61J 1/06* | (2006.01) |
| *A61J 1/20* | (2006.01) |
| *A61K 9/00* | (2006.01) |
| *A61K 9/70* | (2006.01) |
| *A61K 31/122* | (2006.01) |
| *A61K 47/20* | (2006.01) |

(52) U.S. Cl.
CPC ............ *A61M 35/006* (2013.01); *A61J 1/065* (2013.01); *A61J 1/2027* (2015.05); *A61K 9/0014* (2013.01); *A61K 9/7084* (2013.01); *A61K 31/122* (2013.01); *A61K 47/20* (2013.01)

(58) Field of Classification Search
CPC ...... A61M 35/006; A61M 35/00; A61J 1/065; A61J 1/2027; A61J 1/468; A61K 9/0014; A61K 9/7084; A61K 31/122; A61K 47/20; A61K 9/703
USPC ........ 604/289, 290, 304, 306; 424/401, 448, 424/449, 447, 443
See application file for complete search history.

(56) References Cited

U.S. PATENT DOCUMENTS

| | | | | |
|---|---|---|---|---|
| 4,409,988 A | * | 10/1983 | Greenspan ............ | B01L 3/5029 |
| | | | | 435/304.2 |
| 5,476,443 A | * | 12/1995 | Cartmell ............... | A61F 13/023 |
| | | | | 602/57 |
| 5,846,559 A | * | 12/1998 | Hopp ..................... | A61K 9/703 |
| | | | | 424/447 |
| 2002/0185396 A1 | * | 12/2002 | Mainwaring .......... | B65D 25/08 |
| | | | | 206/361 |
| 2010/0055132 A1 | * | 3/2010 | Horn .................. | A61K 31/4745 |
| | | | | 424/231.1 |
| 2013/0115268 A1 | * | 5/2013 | Koo ...................... | A61K 47/00 |
| | | | | 514/772.6 |

* cited by examiner

*Primary Examiner* — Jacqueline F Stephens
(74) *Attorney, Agent, or Firm* — Hugh McTavish

(57) ABSTRACT

Unit dosage forms, devices, and kits for topical delivery of topical immunosensitizers are provided. These include dermal patches, glass swabs, and kits containing a dermal patch and a glass swab. Among other advantages, the unit dosage forms, devices, and kits presented herein deliver a more consistent and controlled volume of drug solution, prevent underdosing and overdosing, prevent or discourage repeat dosing, and provide a more consistent skin area to which the drug solution is applied.

13 Claims, 8 Drawing Sheets

DERMAL PATCHES AND GLASS SWABS FOR APPLICATION OF TOPICAL IMMUNOSENSITIZERS

BACKGROUND

Topical immunosensitizers are compounds that when applied topically to the skin in rather small amounts induce a delayed-type hypersensitivity (DTH) response in a large fraction of persons. Examples of topical immunosensitizers include squaric acid dibutyl ester (SADBE), squaric acid ethyl ester, squaric acid esters generally including monoesters and dieesters, diphenylcyclopropenone (DPCP), 1-chloro-2,4-dinitrobenzene (DNCB), and 1-chloro-2,6-dinitrobenzene. (Buckley et al., Lee et al.)

Poison ivy and its active ingredient urushiol are also topical immunosensitizers.

SADBE and other topical immunosensitizers diphenylcyclopropenone and DNCB have been used successfully to treat common warts and alopecia areata. In these cases, solutions of 0.05% to 2.0% weight/volume are used. Almost always the vehicle is acetone. The immunosensitizers have all been shown to be effective in these uses. For common warts the immunosensitizer is applied to the wart, repeatedly, usually at about weekly intervals, until the wart resolves. For alopecia areata, it is applied to the scalp repeatedly on the affected area, usually weekly, until resolution. (Buckley et al., Lee et al.)

SADBE has also now been shown to be effective to prevent outbreaks of herpes labialis (cold sores or oral herpes) in persons with frequent outbreaks. (Palli et al., Chang et al.) A single dose applied to the arm, not to the lip or lesions, was found to significantly decrease number of cold sore outbreaks for about four months. (Palli et al., Chang et al.) The mechanism appears to be that one dose changes immune gene expression in a systemic way 8 weeks after the one dose, including increasing interferon gamma (IFNG) expression and decreasing interleukin-5 (IL5) expression in peripheral blood mononuclear cells (PBMCs) exposed to herpes simplex virus and other stimuli in vitro (McTavish et al.)

SUMMARY

New unit dosage forms and devices for topical delivery of topical immunosensitizers are needed. Among other advantages, the unit dosage forms, devices, and kits presented herein deliver a more consistent and controlled volume of drug solution, prevent underdosing and overdosing, prevent or discourage repeat dosing, and provide a more consistent skin area to which the drug solution is applied. The unit dosage forms and devices and kits also provide containers for the drug solution that help to keep it stable and unchanged in storage because the containers are completely sealed from air, thus allowing exclusion of water vapor and oxygen that can react with and break down certain topical immunosensitizers, and contact the drug solution with only glass, an inert material that does not react with and is not extracted by the solutions.

Embodiments of the invention provide unit dosage forms of a topical immunosensitizer, and other topically applied drugs, that are stable to storage, can be conveniently and safely and accurately used by an end user patient, avoid contact of the topical drug with unintended skin of the patient, and facilitate dosing of an consistent volume or amount of drug over a consistent skin area.

One embodiment of the invention provides a dermal patch comprising: (a) a backing layer comprising a fabric overlaid by an adhesive over at least part of the area of the fabric; the backing layer overlaid over a portion of its area by (b) an absorbent gauze layer; the absorbent gauze layer comprising a liquid or semi-liquid solution comprising a vehicle and a topical immunosensitizer dissolved in the vehicle.

The term "semi-liquid" here means a viscous but not completely solid composition, including a cream, lotion, or gel.

Another embodiment provides a glass swab comprising: (a) a sealed glass ampoule comprising a liquid solution of a topical immunosensitizer dissolved in a liquid vehicle; and (b) a foam applicator tip attached to the sealed glass ampoule; wherein the sealed glass ampoule can be broken by squeezing by hand by a person of ordinary strength, and wherein the glass swab is adapted so that when the glass ampoule is broken and inverted the liquid solution permeates the foam tip within 5 minutes so that the foam tip upon contacting a surface wets the surface with the liquid solution.

In a specific preferred embodiment the glass swab further comprises (c) a polymer barrier layer surrounding the glass ampoule and sealed to the foam applicator tip, wherein the polymer barrier layer is adapted to prevent broken glass fragments and the liquid solution from penetrating the polymer barrier layer and contacting the skin of fingers of a person breaking the glass swab by squeezing.

Another embodiment provides a method of making a glass swab comprising (a) a sealed glass ampoule comprising a liquid solution of a topical immunosensitizer that is a squaric acid ester dissolved in a liquid vehicle that is dimethylsulfoxide (DMSO), methanol, ethanol, propanol, butanol, isopropanol, isobutanol, acetone, or a combination thereof; and (b) a foam applicator tip attached to the sealed glass ampoule; wherein the sealed glass ampoule can be broken by squeezing by hand by a person of ordinary strength, and wherein the glass swab is adapted so that when the glass ampoule is broken and inverted the liquid solution permeates the foam tip within 5 minutes so that the foam tip upon contacting a surface wets the surface with the liquid solution. The method either comprises (a)(1) treating the vehicle with molecular sieves (preferably under a dry atmosphere) to remove water from the vehicle to produce dried vehicle; and dissolving the squaric acid ester into the dried vehicle (preferably under a dry atmosphere) to produce a dry solution; or (a)(2) dissolving the squaric acid ester into the vehicle to form the solution, then treating the solution with molecular sieves (preferably under a dry atmosphere) to remove water from the vehicle to produce a dry solution. The method further comprises (b) filling the dry solution into the glass ampoule under a dry atmosphere and sealing the glass ampoule to form a gas-tight seal; wherein the dry solution in the ampoule only contacts glass until the gas-tight seal is broken.

Another embodiment provides a kit comprising: (a) a dermal patch comprising: (a)(1) a backing layer comprising a fabric overlaid by an adhesive over at least part of the area of the fabric; the adhesive backing layer overlaid over a portion of its area by (a)(2) an absorbent gauze layer; and (b) a sealed container containing a liquid or semi-liquid solution, the solution comprising a topical immunosensitizer dissolved in a vehicle.

In a preferred embodiment of the kit, the sealed container (b) is a glass swab comprising: (b)(1) a sealed glass ampoule comprising a liquid solution of a topical immunosensitizer dissolved in a liquid vehicle; and (b)(2) a foam applicator tip attached to the sealed glass ampoule; wherein the sealed glass ampoule can be broken by squeezing by hand by a person of ordinary strength, and wherein the glass swab is adapted so that when the glass ampoule is broken and inverted the liquid solution permeates the foam tip within 5 minutes so that the foam tip upon contacting a surface wets the surface with the liquid solution. In a more preferred embodiment, the glass swab further comprises (b)(3) a polymer barrier layer surrounding the glass ampoule and sealed to the foam applicator tip, wherein the polymer barrier layer is adapted to prevent broken glass fragments and the liquid solution from penetrating the polymer barrier layer and contacting the skin of fingers of a person breaking the glass swab by squeezing.

Another embodiment provides a method of topically applying a controlled dose of a topical immunosensitizer comprising: applying and adhering to skin of a human an adhesive dermal patch comprising: a backing layer comprising a fabric overlaid by an adhesive over at least part of the area of the fabric; the backing layer overlaid over a portion of its area by an absorbent gauze layer; the absorbent gauze layer comprising a liquid or semi-liquid solution comprising a vehicle and a topical immunosensitizer dissolved in the vehicle.

Another embodiment provides a kit comprising: (a) a dermal patch comprising: (a)(1) a backing layer comprising a fabric overlaid by an adhesive over at least part of the area of the fabric; the adhesive backing layer overlaid over a portion of its area by (a)(2) an absorbent gauze layer; and (b) a sealed container containing a liquid solution, the solution comprising a topical immunosensitizer dissolved in a vehicle; and (c) an absorbent swab (e.g., a cotton swab).

Another embodiment provides a method of applying a topical immunosensitizer, the method comprising: obtaining a kit comprising: (a) a dermal patch comprising: (a)(1) a backing layer comprising a fabric overlaid by an adhesive over at least part of the area of the fabric; the adhesive backing layer overlaid over a portion of its area by (a)(2) an absorbent gauze layer; and (b) a sealed container containing a liquid solution, the solution comprising a topical immunosensitizer dissolved in a vehicle; and (c) an absorbent swab (e.g., a cotton swab). The method further comprises: opening the sealed container; dipping the absorbent swab in the liquid solution in the container to wet the swab; contacting the wet swab with the absorbent gauze layer of the dermal patch to wet the absorbent gauze layer and produce a loaded dermal patch loaded with the liquid solution; and applying the loaded dermal patch to the skin of a human.

DETAILED DESCRIPTION

Figure 1:
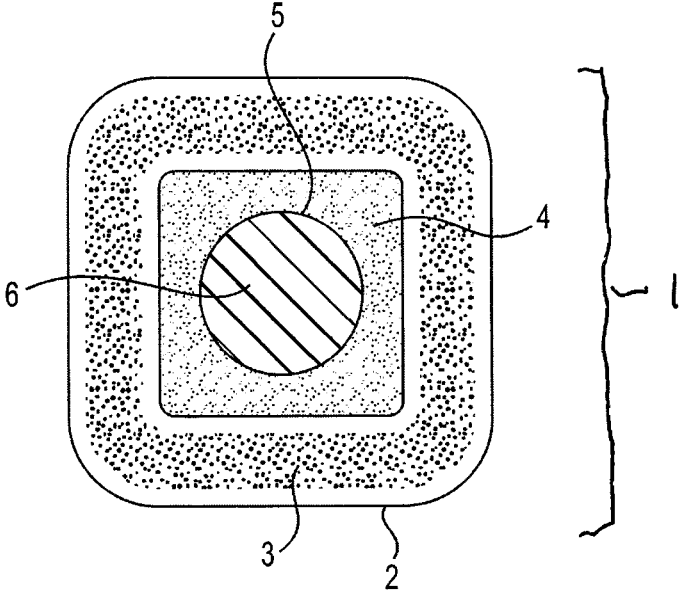
FIG. 1 is a diagram of a dermal patch of the invention

One embodiment of the invention provides a dermal patch comprising: (a) a backing layer comprising a fabric overlaid by an adhesive over at least part of the area of the fabric; the backing layer overlaid over a portion of its area by (b) an absorbent gauze layer; the absorbent gauze layer comprising a liquid or semi-liquid solution comprising a vehicle and a topical immunosensitizer dissolved in the vehicle. An example of this is shown in FIG. 1.

The dermal patch 1 includes a backing layer 2 with an adhesive 3 over at least a portion of the backing layer. The adhesive is for adhering the patch to the skin of the patient. FIG. 1 also shows a barrier layer 4 overlaying the backing layer 2 and adhesive 3 and underlaying an absorbent gauze layer 5. The absorbent gauze 5 optionally comprises a liquid or semi-liquid solution 6 comprising a vehicle and a topical immunosensitizer dissolved in the vehicle.

The backing layer 2 and adhesive 3 and gauze 5 may be conventional materials used in dermal patches such as BAND AID bandages. For example, the backing layer together with the adhesive in one embodiment is 3M Medical Tape 9916 (3M corporation, Saint Paul, MN, USA). In that case, the backing layer is 2.2 oz/yd$_2$ (62 g/m$_2$) 100% Polyester Tan Spunlace Nonwoven, and the adhesive is a pressure-sensitive acrylate adhesive. The barrier layer 4 is optional. In one example it is 3M 9733 polyester film laminate, consisting of a laminate of polyester and an ethylene vinyl acetate copolymer heat seal layer. This is impervious and resistant to dimethylsulfoxide and most other solvents, so that it serves as a barrier to ensure that the DMSO to be added to the gauze portion does not extract adhesive or other component from the patch. The gauze layer 5 may be in one embodiment a polyester, such as Precision Fabrics PFG 0700-00000. Polyester is also resistant to and non-reactive with DMSO and other solvents, which is desirable for the gauze. The absorbent gauze layer in some embodiments may be attached to the barrier layer without adhesives, by for instance sonic welding.

In one embodiment the liquid or semi-liquid solution 6 in the gauze layer 5 is a solution of the topical immunosensitizer squaric acid dibutyl ester (SADBE) dissolved in the vehicle dimethylsulfoxide (DMSO).

Figure 2:
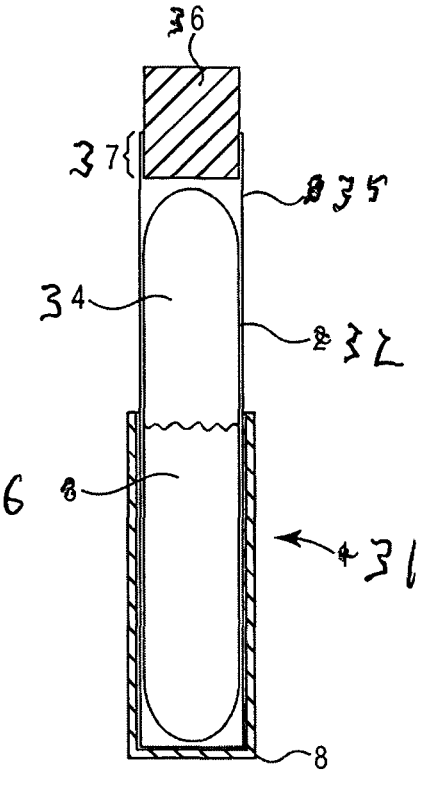
FIG. 2 is a diagram of a glass swab of the invention.

FIG. 2 shows a glass swab 31 of the invention. Glass swab 31 includes a sealed glass ampoule 32 containing a liquid or semi-liquid solution 6 of a topical immunosensitizer dissolved in a vehicle, preferably a liquid vehicle. The sealed glass ampoule also contains a head space 34, which usually contains gas at approximately atmospheric pressure. The gas may be air or an inert gas such as nitrogen or argon. In specific embodiments, the gas is dry, meaning that it has little or no water vapor. Dry gas is desirable if the immunosensitizer is water labile, as SADBE is. Air can be dried, but more typically the dry gas would be an inert gas such as nitrogen or argon. FIG. 2 also shows a barrier layer 35 surrounding the glass ampoule 32. The barrier layer 35 in specific embodiments is impervious to the vehicle that dissolves the topical immunosensitizer and impervious to the immunosensitizer. In specific embodiments, the barrier layer 35 is a polymer, preferably a translucent or more preferably clear polymer. In one embodiment the barrier layer is cellulose acetate butyrate. The glass swab also includes a foam tip 36. In one embodiment, the foam tip is composed of polyolefin. Polyolefin is insoluble in and resistant to DMSO and other solvents, so the DMSO-SADBE solution does not extract anything and is not modified by contact with the foam tip. The foam tip 36 should be sealed with the barrier layer 35, and in FIG. 2 they are sealed along the collar area 37. The seal can be effected by an adhesive or more preferably by direct sealing, such as by heat or sonic welding or by use of a volatile solvent that partially dissolves the barrier layer 35 to allow it to adhere to the foam tip 36 to form a seal.

The barrier layer may comprise more than one material. For instance, it could include a polymer blend or a cardboard layer over a portion of the barrier layer connected to a polymer over another portion of the barrier layer. There may also be a cardboard cap 8 covering one or both ends of the glass swab, as in FIG. 2. In FIG. 2 one carboard cap 8 is shown covering the bottom end of the glass swab. It could be a reversible and removable cardboard cap that in shipping covers the foam tip 36, and is removed by the user and repositioned over the other end of the glass swab before the user squeezes through both the cardboard and the barrier layer to break the glass ampoule.

When the glass ampoule is broken, the solution 6 leaks out of the glass ampoule but is restricted by the barrier layer so no glass fragments and no solution contacts the skin of the user's fingers. The user should then invert the glass swab after breaking it, to allow the solution 6 to permeate the foam tip 36. The user may also squeeze the glass swab after breaking it to speed the process of the solution permeating the foam tip. When the foam tip is permeated with the solution, the user may dab or wipe the foam tip onto the user's skin to apply the solution to the skin, or may dab or wipe the foam tip onto the gauze portion of the dermal patch to put the solution into the absorbent gauze layer, and may then apply the dermal patch to the user's skin to dose the solution onto the user's skin.

Either with or without the dermal patch, the glass swab facilitates administering a rather defined amount of immunosensitizer solution. It also helps avoid delivering too much solution and avoid the solution dripping from where it is applied so that it contacts non-target areas such as the fingers. And it provides a single use container that is visibly broken and damaged after one use so patients are less likely to try to reuse the container for multiple doses over time, which would be overdosing. It accomplishes these because it takes about 30-60 seconds for the drug solution to penetrate the foam tip so the tip can be used to wet another surface, and the foam tip is initially and for a few minutes not saturated, so it is difficult, and initially impossible to drip solution onto a user's skin or a patch, which is to be avoided since that results in more than the intended dose and dripping of the solution onto non-target areas. The glass swab is visibly broken with broken glass after a single use. That makes it less likely a patient at home will try to use the same glass swab to dose themselves again on subsequent doses, which is not intended for the SADBE-DMSO solution in preventing herpes labialis outbreaks, where it has been shown that a single dose to the arm prevents outbreaks for 3 months or more (Palli et al., Chang et al.), and that a single dose to the arm causes significant systemic immune changes 8 weeks after the single dose (McTavish et al.). Also, SADBE is rather unstable in the presence of even small amounts of water in the DMSO solution, and DMSO picks up water from the air when it is exposed to air, so after breaking the package it is not desired that the user would reuse the container because the concentration of SADBE will decrease markedly over time due to uptake of water into the solution and hydrolysis. With the cellulose acetate butyrate barrier layer in the glass swab, an additional visible signal is provided that discourages repeat usage. The cellulose acetate butyrate layer turns from clear to white over about 60 minutes after the glass swab is broken and the DMSO-SADBE solution contacts the cellulose acetate butyrate. Other polymers in the barrier layer would likely have the same property of changing appearance to appear visibly damaged after contact with DMSO or other vehicles for the immunosensitizer.

The dermal patch, either separately or in combination with the glass swab, also has the same advantages as the glass swab: It promotes consistent dosing in terms of volume of immunosensitizer solution applied and in terms of skin area over which the drug is applied. It also helps avoid delivering too much solution and avoid the solution dripping from where it is applied so that it contacts non-target areas such as the fingers. And it provides a single use application device that basically cannot be used for a second dose, thus making it less likely patients would try to apply multiple doses with the same patch or the same kit containing a single dermal patch and a container of liquid or semi-liquid topical immunosensitizer solution, whether the container is a glass swab or not.

EMBODIMENTS

In one embodiment of the dermal patch, the absorbent gauze comprises a polyester.

In specific embodiments of the dermal patches, glass swabs, kits, and methods, the topical immunosensitizer comprises a squaric acid ester, diphenylcyclopropenone, 1-chloro-2,4-dinitrobenzene (DNCB), 1-chloro-2,6-dinitrobenzene, or urushiol.

In specific embodiments, the immunosensitizer is SADBE.

In certain embodiments, the vehicle comprises a cream, a lotion, acetone, mineral oil, petroleum jelly, dimethylsulfoxide (DMSO), acetone, propanol, isopropanol, n-butanol, isobutanol, ethanol, or methanol. In specific embodiments it comprises DMSO, acetone, ethanol, or isopropanol. In specific embodiments the vehicle comprises DMSO. In other specific embodiments, the vehicle comprises DMSO, methanol, acetone, ethanol, propanol, isopropanol, butanol, isobutanol, water, or combinations thereof.

In specific embodiments, the vehicle is DMSO and the topical immunosensitizer is SADBE dissolved at 0.1% to 5% (wt./vol.) in the DMSO.

In specific embodiments of the dermal patches, the absorbent gauze layer is attached permanently to the adhesive backing layer (either directly or indirectly through a barrier layer).

In other specific embodiments, the absorbent gauze layer is not attached to the adhesive backing layer.

In specific embodiments of the glass swab, the glass swab comprises one or more barrier layers partially or fully surrounding the glass ampoule and adapted to prevent broken glass fragments and the liquid solution from penetrating the on or more barrier layers and contacting skin of a person holding the glass swab, except liquid solution through the foam tip.

In particular embodiments, the barrier layer comprises a polymer barrier layer, for example cellulose acetate, cellulose acetate butyrate, polyester, or polyethylene.

In particular embodiments, the glass swab comprises a polymer barrier layer partially or fully surrounding the glass ampoule and sealed to the foam applicator tip, wherein the polymer barrier layer is adapted to prevent broken glass fragments and the liquid solution from penetrating the polymer barrier layer and contacting the skin of fingers of a person breaking the glass swab by squeezing.

In specific embodiments of the dermal patch, glass swab, methods, and kits of the invention, the vehicle is selected from DMSO, methanol, acetone, ethanol, propanol, isopropanol, butanol, isobutanol, water, and combinations thereof.

In specific embodiments of the dermal patch, glass swab, methods, and kits of the invention, the topical immunosensitizer is a squaric acid ester (for example SADBE) and the vehicle is DMSO, methanol, ethanol, propanol, butanol, isopropanol, isobutanol, acetone, or a combination thereof.

In a specific embodiment of the dermal patch, glass swab, methods, and kits of the invention, the vehicle is DMSO and the topical immunosensitizer is SADBE. The glass swab is particularly advantageous for this combination, because the sealed glass ampoule provides a permanent gas-tight seal that excludes air and water vapor, and the glass ampoule can be filled with nitrogen or another inert gas or dry air to limit water vapor, which is advantageous because DMSO avidly acquires water content from air and this must be avoided because SADBE is readily hydrolyzed by water and unstable in DMSO solutions with high water content. Also, DMSO is an excellent solvent that extracts or dissolves many substances, including many polymers, but glass is completely resistant to DMSO.

In specific embodiments of he glass swab, the barrier layer or layers comprise a cellulose polymer layer (e.g., cellulose acetate or cellulose acetate butyrate) and/or a cardboard layer.

In specific embodiments of the glass swab, particularly where the immunosensitizer is SADBE or a squaric acid ester, the solution has less than 100 ppm water, or more preferably less than 50 ppm, less than 20 ppm, or less than 10 ppm water.

In specific embodiments of the glass swab, the solution in the glass ampoule only contacts glass until the glass ampoule is broken.

One embodiment of the invention is a method of making a glass swab of the invention comprising: (a) treating the vehicle (e.g., DMSO or acetone) with molecular sieves under a dry atmosphere to remove water from the vehicle to produce dried vehicle; (b) dissolving the topical immunosensitizer (e.g., SADBE) into the dried vehicle under a dry atmosphere to produce a dry solution; and (c) filling the dry solution into the glass ampoule and sealing the glass ampoule to form a gas-tight seal; wherein the solution only contacts glass until the gas-tight seal is broken. Preferably step (c) is filling the dry solution under a dry atmosphere (e.g., nitrogen, argon, or dried air) into the glass ampoule and sealing the glass ampoule to form a gas-tight seal.

One embodiment of the invention provides a method of making the glass swab comprising: (a)(1) treating the vehicle (e.g., DMSO or acetone) with molecular sieves (preferably under a dry atmosphere) to remove water from the vehicle to produce dried vehicle; and dissolving the squaric acid ester into the dried vehicle (preferably under a dry atmosphere) to produce a dry solution; or (a)(2) dissolving the squaric acid ester into the vehicle (e.g., DMSO or acetone) to form the solution, then treating the solution with molecular sieves (preferably under a dry atmosphere) to remove water from the vehicle to produce a dry solution. The method further comprises (b) filling the dry solution into the glass ampoule under a dry atmosphere (e.g., nitrogen, argon, or dried air) and sealing the glass ampoule to form a gas-tight seal; wherein the dry solution in the ampoule only contacts glass until the gas-tight seal is broken.

Another embodiment provides a kit comprising: (a) dermal patch comprising: an adhesive backing layer comprising a fabric overlaid by an adhesive over at least part of the area of the fabric; the adhesive backing layer overlaid over a portion of its area by an absorbent gauze layer; and (b) a sealed container containing a liquid or semi-liquid solution, the solution comprising a topical immunosensitizer dissolved in a vehicle.

In specific embodiments of the kit, the dermal patch further comprises a barrier layer between the gauze layer and the adhesive backing layer, wherein the barrier layer is impervious to the vehicle and the topical immunosensitizer.

In specific embodiments, the sealed container is a glass swab of the invention. The sealed container can also be another type of container, such as a plastic vial with a screw cap, a glass vial with a screw cap, or a sealed plastic vial with a neck that can be broken by hand.

In specific embodiments of the kit the sealed container is adapted to be opened by hand without tools by a person.

Another embodiment of the invention provides a method of topically applying a controlled dose of a topical immunosensitizer comprising: applying and adhering to skin of a human an adhesive dermal patch comprising: a backing layer comprising a fabric overlaid by an adhesive over at least part of the area of the fabric; the backing layer overlaid over a portion of its area by an absorbent gauze layer; the absorbent gauze layer comprising a liquid or semi-liquid solution comprising a vehicle and a topical immunosensitizer dissolved in the vehicle.

The topically applying is usually for medically treating a person with the topical immunosensitizer, such as to prevent herpes episodes, or to treat common warts.

In specific embodiments of topically applying a controlled dose of a topical immunosensitizer, the method further comprises before the applying step, opening a unit dose container containing a liquid or semi-liquid solution comprising a vehicle and a topical immunosensitizer dissolved in the vehicle, and applying the solution to the absorbent gauze layer of the dermal patch to form the absorbent gauze layer comprising the liquid or semi-liquid solution comprising the vehicle and the topical immunosensitizer dissolved in the vehicle. In this case, the absorbent gauze layer did not contain the topical immunosensitizer solution before the step of applying the solution to the absorbent gauze layer of the dermal patch.

One embodiment comprises a kit comprising: (a) dermal patch comprising: (i) an adhesive backing layer comprising a fabric overlaid by an adhesive over at least part of the area of the fabric; the adhesive backing layer overlaid over a portion of its area by (ii) an absorbent gauze layer; and (b) a sealed container containing a liquid or semi-liquid solution, the solution comprising a topical immunosensitizer dissolved in a vehicle.

In a more specific embodiment, the sealed container is a glass swab comprising: (i) a sealed glass ampoule comprising a liquid solution of a topical immunosensitizer dissolved in a liquid vehicle; and (ii) a foam applicator tip attached to the sealed glass ampoule; wherein the sealed glass ampoule can be broken by squeezing by hand by a person of ordinary strength, and wherein when the glass ampoule is broken and inverted the liquid solution permeates the foam tip within 5 minutes so that the foam tip upon contacting a surface wets the surface with the liquid solution.

Figure 6:
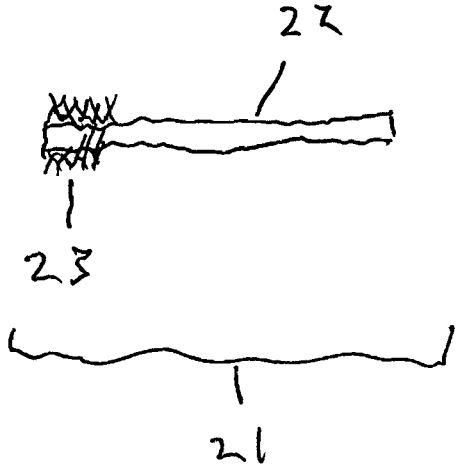
FIG. 6. An absorbent swab.

In another embodiment of the kit, the kit further comprises an absorbent swab. An example of the absorbent swab is shown in FIG. 6. An example of the absorbent swab is a cotton swab, for instance a Q-TIP brand swab. The swab 21 is typically a short stick 22 about 3 to 10 cm in length with one or both ends of the stick covered in an absorbent material 23, which may be, for example a foam or a network of fibers. The foam and fibers can be made of any suitable material, including cotton and polymers such as polyurethane or polyester.

Figure 7:
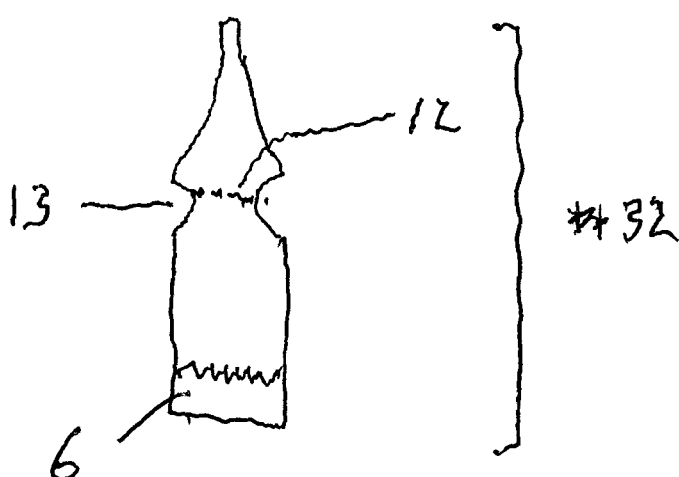
FIG. 7. A glass ampoule with a scored ring containing the topical immunosensitizer solution.

In one embodiment of the kit, the sealed container is a sealed glass ampoule. It can contain a semi-liquid or preferably a liquid solution of a topical immunosensitizer dissolved in a vehicle. The ampoule in a preferred embodiment has a scored break ring in the glass to facilitate breaking the ampoule by hand at the scored ring. An example of the ampoule is shown in FIG. 7 showing glass ampoule 32 with scored ring 12 on the neck 13 of the ampoule. The diameter at ring 12 is preferably sufficient to allow dipping an absorbent swab, such as a standard cotton swab, in the container through the broken neck at ring 12 without squeezing the swab, e.g., at least about 7 mm or about 7 to 20 mm.

Figure 8:
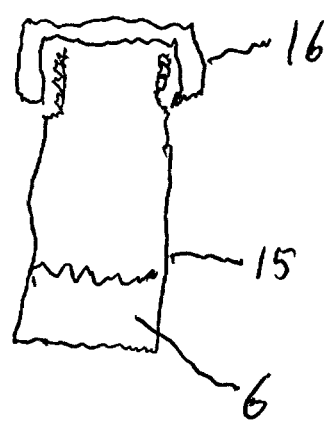
FIG. 8. A vial with a screw cap containing the topical immunosensitizer solution.
Figure 9:
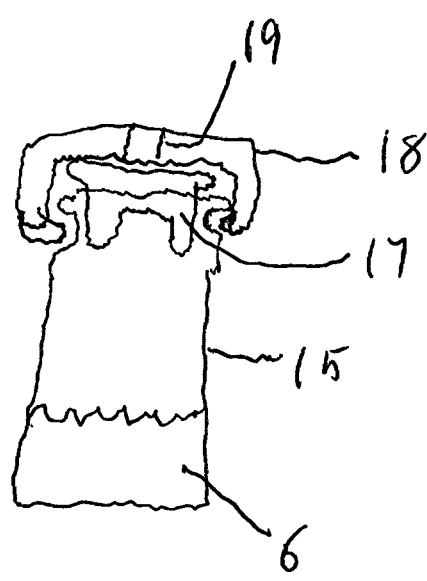
FIG. 9. A vial with a crimp cap containing the topical immunosensitizer solution.

In another embodiment of the kit, the sealed container is a glass vial with a screw cap or with a stopper held by a tear-off crimp cap. FIG. 8 shows vial 15 with screw cap 16. FIG. 9 shows vial 15 with stopper 17 held by tear-off crimp cap 18 with perforations 19 for tearing the crimp cap.

In some embodiments of the kit with the absorbent swab, the swab has at least one end covered with an absorbent material capable of absorbing the liquid solution and having a maximum capacity that is the volume of the liquid solution the one end is capable of absorbing, and the volume of liquid solution in the sealed container is about half to about one-and-a-half times the maximum capacity of the at least one end.

In other embodiments of the kit, the volume of liquid solution in the sealed container is 100 to 350 microliters.

Another embodiment provides a method of applying a topical immunosensitizer, the method comprising: obtaining a kit comprising: (a) a dermal patch comprising: (a)(1) a backing layer comprising a fabric overlaid by an adhesive over at least part of the area of the fabric; the adhesive backing layer overlaid over a portion of its area by (a)(2) an absorbent gauze layer; and (b) a sealed container containing a liquid solution, the solution comprising a topical immunosensitizer dissolved in a vehicle; and (c) an absorbent swab (e.g., a cotton swab). The method further comprises: opening the sealed container; dipping the absorbent swab in the liquid solution in the container to wet the swab; contacting the wet swab with the absorbent gauze layer of the dermal patch to wet the absorbent gauze layer and produce a loaded dermal patch loaded with the liquid solution; and applying the loaded dermal patch to the skin of a human.

In a more specific example of this method, the sealed container is a sealed glass ampoule containing a liquid solution of a topical immunosensitizer dissolved in a liquid vehicle, the container having a scored break ring in the glass to allow breaking the ampoule by hand at the scored ring; wherein the step of opening the sealed container comprises breaking the sealed glass ampoule by hand.

In another specific example of the method with the absorbent swab, the stop of dipping the absorbent swab in the liquid solution absorbs more than half of the volume of the liquid solution in the container.

In a more specific method, the step of contacting the wet swab with the absorbent gauze layer visibly wets 80 to 100% of the area of the absorbent gauze layer.

Another embodiment provides a method of topically applying a controlled dose of a topical immunosensitizer comprising: (1) applying and adhering to skin of a human an adhesive dermal patch comprising: (a) a backing layer comprising a fabric overlaid by an adhesive over at least part of the area of the fabric; the backing layer overlaid over a portion of its area by (b) an absorbent gauze layer; the absorbent gauze layer comprising a liquid or semi-liquid solution comprising a vehicle and a topical immunosensitizer dissolved in the vehicle.

In a more specific embodiment, this method further comprises before the applying step, opening a unit dose container containing a liquid or semi-liquid solution comprising a vehicle and a topical immunosensitizer dissolved in the vehicle, and applying the solution to the absorbent gauze layer of the dermal patch to form the absorbent gauze layer comprising the liquid or semi-liquid solution comprising the vehicle and the topical immunosensitizer dissolved in the vehicle. In a more specific embodiment of that method, after the opening step the method comprises dipping an absorbent swab in the liquid or semi-liquid solution to wet the absorbent swab; and the step of applying the solution to the absorbent gauze layer comprises contacting the wetted absorbent swab with the gauze layer to visibly wet the gauze over 80% to 100% of the area of the absorbent gauze layer.

In specific embodiments, the the solution is a liquid solution and the step of dipping the absorbent swab in the liquid solution absorbs more than half of the volume of the liquid solution in the container onto the absorbent swab.

In specific embodiments of the methods of topically applying a controlled dose of a topical immunosensitizer, the unit dose container is a glass swab comprising: (a) a sealed glass ampoule comprising a liquid solution of a topical immunosensitizer dissolved in a liquid vehicle; and (b) a foam applicator tip attached to the sealed glass ampoule; wherein the sealed glass ampoule can be broken by squeezing by hand by a person of ordinary strength, and wherein when the glass ampoule is broken and inverted the liquid solution permeates the foam tip within 5 minutes so that the foam tip upon contacting a surface wets the surface with the liquid solution. In specific embodiments, the method comprises: (1) breaking the glass ampoule by hand and inverting the glass swab to permeate the foam tip with the liquid solution; and (2) contacting the foam tip with the gauze layer to visibly wet the gauze over 80% to 100% of the area of the absorbent gauze layer.

In specific embodiments of the methods of applying, the vehicle is DMSO and the topical immunosensitizer is SADBE.

EXAMPLES

Example 1

A Placebo-Controlled Phase 1 Clinical Trial Shows that SADBE Extends Time to Next Outbreak in Subjects with Frequent Herpes Labialis Outbreaks Methods This exploratory, double-blind, randomized placebo-controlled study was conducted between November 2013 and September 2015 at Massachusetts General Hospital. Healthy adults, ages 18 to 69 years, who self-reported having 6 or more episodes of herpes labialis in the previous 12 months received a topical sensitization dose on the arm at the initial visit, and then received a topical treatment dose applied to a lesion during the first 2 herpes labialis episodes occurring at least 2 weeks after the sensitization dose. Participants were randomized 1:1:1 to receive dimethyl sulfoxide alone (placebo), 2.0% SADBE sensitization and 0.5% SADBE treatment doses, or 2.0% SADBE sensitization, 0.2% SADBE treatment doses. The study was approved by Partners Human Research Committee institutional review board, and all participants provided their written informed consent (clinicaltrials.gov identification No. NCT01971385).
Results. Fifty-four patients were enrolled into the study; 43 patients had at least 1 form of contact (either in person or by phone) with research staff following the sensitizing dose and were included in the efficacy data analysis. The data analyzed involves 9 males and 34 females.

Figure 3:
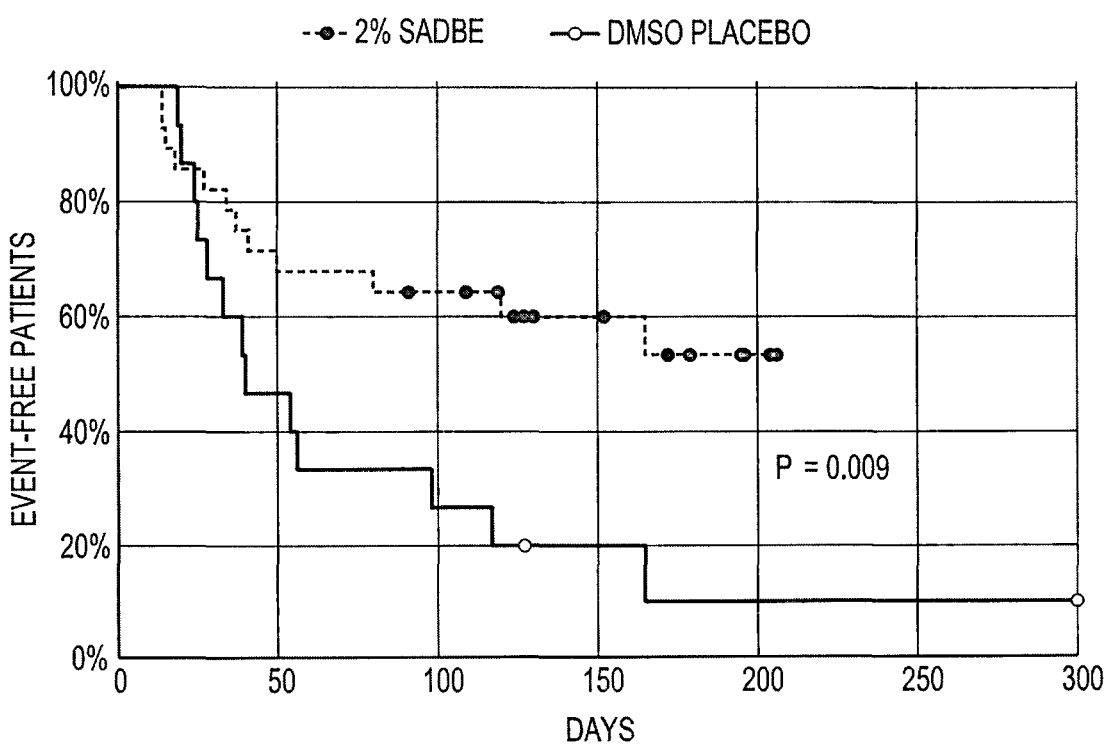
FIG. 3. Days to First New Herpes Labialis Outbreak Following the Sensitization Dose. This Kaplan-Meier graph shows the time-to-event curve of percent of subjects without a new herpes labialis outbreaks for the indicated number of days after the sensitization dose. Circles along the curves represent censored observations.

One planned primary end point was days to the next herpes labialis outbreak after the last treatment dose. However, 16 of 28 patients who received 2.0% SADBE for sensitization did not experience another outbreak and did not receive a subsequent treatment dose after sensitization. Thus, we analyzed time to next outbreak after the sensitization dose. Data from patients who never experienced a first outbreak following sensitization were censored on the last available follow-up date and Kaplan-Meier time-to-event curves were estimated and graphed (FIG. 3). The median time to event for the placebo group was 40 days versus more than 122 days for the 2.0% SADBE group, which difference was highly significant (P=0.009).
Aside from autosensitization dermatitis that occurred in 1 patient after being exposed to the SADBE sensitization dose for 24 hours, the only other adverse events noted were itching and redness at the sensitization site, which was seen in 13 patients who received 2.0% SADBE and 2 patients who received placebo.
Discussion This study suggests that sensitization of patients with SADBE may be useful in preventing herpes simplex virus outbreaks. Our initial hypothesis was that treatment of an active lesion would be necessary to achieve the appropriate immunologic response, but our results suggest this additional step may not be necessary. Overall, SADBE was well tolerated by our patients. (Palli et al.)

Example 2

Immune Characteristics Correlating with HSV-1 Immune Control and Effect of Squaric Acid Dibutyl Ester on Immune Characteristics of Subjects with Frequent Herpes Labialis Episodes Introduction: Differences in immune characteristics, including immune gene expression by peripheral blood mononuclear cells (PBMCs), correlating with herpes labialis and good or poor immune control of herpes simplex virus type 1 (HSV-1) (i.e., frequency of herpes labialis episodes), and how these characteristics change after dosing with squaric acid dibutyl ester (SADBE), were investigated.
Methods: PBMCs were collected from persons positive for IgG against HSV-1 and having frequent (self-reported 6 or more episodes in the prior 12 months), infrequent (1 or 2 episodes in the prior 12 months), or no herpes labialis outbreaks in the prior 12 months. The PBMCs were tested for proliferation against HSV-1 and a fungal antigen (*Candida*) and immune gene expression in the presence of HSV-1 and *Candida*. On day 1 after blood collection the subjects with frequent outbreaks were dosed topically on the arm once with 2% SADBE in DMSO, and their PBMCs were collected and tested 2 weeks later and 8 weeks later.

Doses were applied by dipping a cotton swab in a 1-ml vial of liquid study medication, then swabbing a spot on the inner aspect of the upper arm over an area of about 10 to 15 mm diameter encircled by petroleum jelly. After application, the spot was covered by TEGADERM™ dressing, and subjects were advised to remove the dressing and wipe the spot with a wet cloth 3 hours later. The weight of the vial of study medication with the vial standing in it was measured immediately before and immediately after dosing each subject. The difference was the net mass of drug applied. In most cases, 10 mg to 20 mg of drug solution was applied to the arm.
Results: Those with good immune control of their HSV-1 infection (fewer outbreaks) differ from those with poorer immune control in these ways: (1) Greater PBMC proliferation in vitro to HSV-1, HSV-1-infected cell extracts, and *Candida* considered together (P<0.01). (2) Higher expression of interferon gamma (IFNG) and five other immune-related genes (P<0.05 for each) and lower expression of interleukin-5 (IL5) and two other immune-related genes (P<0.05 for each) in PBMCs in vitro stimulated with heat-inactivated HSV-1 virus.

The subjects with frequent outbreaks were treated once with SADBE, and 56 days later the PBMCs of these subjects differed from PBMCs from the same subjects taken on day 1 before treatment in exactly the same ways listed above as differences between those with good and poor immune control of HSV-1, and at the same levels of significance. However, at 2 weeks after the one dose, the PBMCs did not differ from PBMCs collected at day 1 in almost any of these gene expression or proliferation measures. Thus, it took more than 2 weeks but less than 8 weeks for the immune system changes to be induced by the single dose of 2% SADBE in DMSO topically applied to the arm.
Conclusions: Higher interferon gamma (IFNG) and lower interleukin-5 (IL5) expression by PBMCs in the presence of HSV-1 correlate with fewer herpes labialis outbreaks, and a single topical dose of 2% SADBE in DMSO to the arm of subjects with frequent herpes labialis episodes improves immune response to HSV-1 by, among other changes, increasing IFNG expression and decreasing IL5 expression in PBMCs in the presence of HSV-1 virus. (McTavish et al.)

Example 3

A Phase 2, Multi-Center, Placebo-Controlled Study of Single Dose Squaric Acid Dibutyl Ester (SADBE) to Reduce Frequency of Outbreaks in Subjects with Recurrent Herpes Labialis After institutional review board approval and written informed consent, this study was conducted at five centers in subjects with four or more herpes labialis episodes in the previous 12 months. Subjects were randomized to receive either (1) one dose of 2% SADBE in DMSO on day 1, (2) 2% SADBE on day 1 and a second lower dose (0.5%) "booster" on day 22, or (3) dimethylsulfoxide (DMSO) vehicle only on days 1 and 22. All subjects were followed for 1 year.

Doses were applied by dipping a cotton swab in a blindly labeled 1 ml vial of liquid study medication, then swabbing a spot on the inner aspect of the upper arm over an area of about 10 to 15 mm diameter encircled by petroleum jelly. After application, the spot was covered by TEGADERM™ dressing, and subjects were advised to remove the dressing and wipe the spot with a wet cloth 3 hours later. The weight of the vial of study medication with the vial standing in it was measured immediately before and immediately after dosing each subject. The difference was the net mass of drug applied. In most cases, 10 mg to 20 mg of drug solution was applied to the arm.

Eligible subjects (n=140) enrolled with median number of outbreaks of 6 (mean=7.8) in the prior 12 months. The 1-dose group was superior to the placebo group in time to next outbreak from day 43 to 121 (p=0.024) (FIG. 1), mean number of outbreaks in days 43-121 in 1-dose (0.231±0.125 standard error) vs. placebo (0.610±0.068) (p=0.011), and proportion of subjects with an outbreak in days 43-121 in 1-dose (9/39=23%) vs. placebo (19/41=46%) (p=0.036). Average number of moderate or severe outbreaks over days 43-121 was also reduced in subjects receiving 1 dose of SADBE (0.128±0.339) vs. placebo (0.390±0.703) (p=0.04), as well as over days 1-365 in 1-dose (0.641±0.931) vs. placebo (1.341±1.76) (p=0.04).

Notably, the 2-dose group was superior to placebo these same measures, but not significantly so. Why the 1-dose may be superior to the 2-dose regimen remains to be investigated, but we hypothesize that the second dose at lower concentration may "tolerize" or down-regulate the immune changes from the 2% SADBE in the first dose.

The largest improvements observed in the SADBE treated groups occurred within days 43-121 of the study. One possible reason may be that SADBE takes about 6 weeks to exert maximal effect on the immune system, and the effects begin to taper off at about 3 to 4 months after the first dose.

The most common adverse event type was administration site reactions, which were all mild or moderate, and all resolved within 3 months, suggesting a favorable risk-benefit profile for topical 2% SADBE in high frequency herpes labialis.

Example 4

A Non-GLP Study to Evaluate Skin Irritation Potential and Residual Drug Levels Following Application of SADBE Dermal Patches to a Swine Model.

American Preclinical Services Study ID STUDY ID: JLM001-PH50

Introduction

Squaric acid dibutyl ester (SADBE) at 2% (w/v) concentration in dimethylsulfoxide (DMSO) was added to a skin patch for dermal dosing of SADBE to test for a delayed-type hypersensitivity response or other skin irritation and to test how much SADBE disappears from the patch with different volumes and time of exposure, and is therefore presumed to enter the skin.

One purpose of this study was to determine the time course of drug elution from the dermal patches into the skin. For that purpose, patches were applied to the skin of pigs and removed 1, 3, 6, or 24 hours later, and then extracted to determine the amount of residual SADBE drug remaining in the patch. The missing SADBE from the amount originally loaded onto the patch is presumed to have transferred into the pig skin.

An additional purpose was to assess immediate and delayed skin irritation, including erythema and edema on the pig skin over 4 weeks after dosing.

Materials and Methods

The skin patches consisted of a polymer backing layer similar to 3M 9916 polyester nonwoven backing layer with adhesive, 3M 9733 polyester film laminate barrier layer, and Precision Fabrics Group 0700-00010 polyester gauze layer. The gauze was heat sealed to the barrier layer. The gauze patch area was about 3 cm².

Patches were removed from the pigs at the indicated times and immediately the reservoir portion of the patch was cut out and placed in a 50 ml tube with 10 ml of DMSO.

Immediately after removing the patch, a kimwipe was used to swab the spot on the pig where the patch had been in order to attempt to recover any SADBE that was on the surface of the skin and had not absorbed into the skin. After wiping with the kimwipe, the kimwipe was placed in a separate 50 ml tube containing 10 ml of DMSO.

The tubes of DMSO with patches or kimwipe were transported to our laboratory, shaken at 200 rpm for 10 minutes, and then the DMSO from each tube was placed in an injection vial and analyzed for SADBE content by HPLC on a C18 column with the program SADBE3-50 ul. SADBE elutes in this program at about 24.0 minutes and absorbs at 255 nm, so the area of the 24.0 min peak at 255 nm was used to quantify SADBE.

The HPLC program details are these:
This program is called SADBE3-50 ul on the HPLC, with 50 ul injection.
Column: USP L1 (ODS), 250 mm×4.6 mm, 5 um (C18)
    Agilent part number 880995-902
Mobile phase: A: 25 mM $KH_2PO_4$ (pH5) (not pH adjusted)
    B: Methanol
Flow rate: 1.0 mL/min
Wavelength: 255 nm, 215 nm
Temperature: Room Temperature
Injection volume: 50 ul

TABLE 1

| Gradient elution: | | |
|---|---|---|
| Time (min) | Eluant A (%) | Eluant B (%) |
| 0 | 95 | 5 |
| 5 | 95 | 5 |
| 10 | 50 | 50 |
| 30 | 20 | 80 |
| 30.1 | 95 | 5 |
| 35 | 95 | 5 |

Results

On Aug. 6, 2018, the first set of patches was placed on 3 pigs. The patches were all held in place on the pigs by an elastic bandage wrapped around the torso of each of the pigs over the patches. The results are shown in Table 2. The net HPLC area of SADBE lost and presumed in skin is calculated as the area predicted from the 20 ul and 50 ul controls minus the observed HPLC area of SADBE extracted from the test patch that was applied to skin.

TABLE 2

| | | | | | SADBE area, 255 nm, 24 min. | SADBE | net HPLC area of SADBE | Percent of SADBE |
|---|---|---|---|---|---|---|---|---|
| Patch number | Pig # | Side | volume on patch | patch removal time hours | In 20180806 | area in kimwipe swab | lost and presumed in skin | presumed in skin |
| | | | | | SADBE content of patches from day 1. | | | |
| 1 | 1 | L | 20 ul | 1 | 1941 | 35 | 1452 | 42.8 |
| 8 | 2 | R | 20 ul | 1 | 1838 | 39 | 1555 | 45.8 |
| 2 | 1 | L | 20 ul | 3 | 735 | 38 | 2658 | 78.3 |
| 7 | 2 | R | 20 ul | 3 | 954 | 44 | 2439 | 71.9 |
| 3 | 1 | L | 20 ul | 6 | 265 | 40 | 3128 | 92.2 |
| 6 | 2 | R | 20 ul | 6 | 244 | 50 | 3149 | 92.8 |
| 4 | 1 | L | 20 ul | 24 | 182 | 19 | 3211 | 94.6 |
| 5 | 2 | R | 20 ul | 24 | 151 | 21 | 3242 | 95.5 |
| 9 | 2 | L | 50 ul | 1 | 5108 | 78 | 3141 | 38.1 |
| 16 | 1 | R | 50 ul | 1 | 4698 | 75 | 3551 | 43.0 |
| 10 | 2 | L | 50 ul | 3 | 2707 | 52 | 5542 | 67.2 |
| 15 | 1 | R | 50 ul | 3 | 1741 | 78 | 6508 | 78.9 |
| 11 | 2 | L | 50 ul | 6 | 1243 | 50 | 7006 | 84.9 |
| 14 | 1 | R | 50 ul | 6 | 666 | 45 | 7583 | 91.9 |
| 12 | 2 | L | 50 ul | 24 | 224 | 20 | 8025 | 97.3 |
| 13 | 1 | R | 50 ul | 24 | 128 | 22 | 8121 | 98.4 |
| 17 | 3 | L | 80 ul | 1 | 9952 | 105 | 3246 | 24.6 |
| 24 | 3 | R | 80 ul | 1 | 9208 | 98 | 3990 | 30.2 |
| 18 | 3 | L | 80 ul | 3 | 9517 | 53 | 3681 | 27.9 |
| 23 | 3 | R | 80 ul | 3 | 6734 | 130 | 6464 | 49.0 |
| 19 | 3 | L | 80 ul | 6 | 2192 | 208 | 11006 | 83.4 |
| 22 | 3 | R | 80 ul | 6 | 2471 | 78 | 10727 | 81.3 |
| 20 | 3 | L | 80 ul | 24 | 509 | 24 | 12689 | 96.1 |
| 21 | 3 | R | 80 ul | 24 | 273 | 20 | 12925 | 97.9 |
| 20 ul patch control | | | | | 3397 | | | |
| 20 ul patch control | | | | | 3391 | | | |
| 50 ul patch control | | | | | 8229 | | | |
| 50 ul patch control | | | | | 8269 | | | |
| 20 ul 2% in 10 ml DMSO on 8/7 | | | | | 3284 | | | |
| 20 ul 2% in 10 ml DMSO on 8/7 | | | | | 3327 | | | |

The controls show that recovery of the SADBE from the patches was complete with this procedure of extracting the patch reservoir into 10 ml DMSO.

Week 2

SADBE patch testing on pigs 4 and 5 was done on Aug. 13, 2018. In this case, patches on both pigs were covered with TEGADERM™, and on one pig the TEGADERM™ was further covered by an elastic bandage as on August 6.

TABLE 3

| | | | | | | net | | |
| | | | | | SADBE | HPLC | Percent | |
| | | | | patch | area, | area of | of | |
| | | | volume | removal | 255 nm, | SADBE | SADBE | |
| Patch | | | on | time | 24 min. In | lost and | presumed | Ace |
| number | Pig # | Side | patch | hours | 20180813 | presumed in skin | in skin | bandage? |
|---|---|---|---|---|---|---|---|---|
| 25 | 4 | L | 20 ul | 3 | 1327 | 2021 | 60.4 | no |
| 26 | 4 | L | 20 ul | 3 | 2076 | 1272 | 38.0 | no |
| 27 | 5 | R | 20 ul | 6 | 328 | 3020 | 90.2 | yes |
| 28 | 5 | R | 20 ul | 6 | 390 | 2958 | 88.4 | yes |
| 29 | 5 | R | 20 ul | 3 | 753 | 2595 | 77.5 | yes |
| 30 | 5 | R | 20 ul | 3 | 842 | 2506 | 74.9 | yes |
| 31 | 4 | L | 20 ul | 6 | 388 | 2960 | 88.4 | no |
| 32 | 4 | L | 20 ul | 6 | 986 | 2362 | 70.5 | no |
| 33 | 4 | R | 50 ul | 3 | 4058 | 4184 | 50.8 | no |
| 34 | 4 | R | 50 ul | 3 | 3549 | 4693 | 56.9 | no |
| 35 | 5 | L | 50 ul | 6 | 1949 | 6293 | 76.4 | yes |
| 36 | 5 | L | 50 ul | 6 | 1376 | 6866 | 83.3 | yes |
| 37 | 5 | L | 50 ul | 3 | 3484 | 4758 | 57.7 | yes |
| 38 | 5 | L | 50 ul | 3 | 5599 | 2643 | 32.1 | yes |
| 39 | 4 | R | 50 ul | 6 | 2454 | 5788 | 70.2 | no |
| 40 | 4 | R | 50 ul | 6 | 3717 | 4525 | 54.9 | no |
| 20 ul patch control | | | | | 3348 | | | |
| 20 ul patch control | | | | | 3348 | | | |
| 50 ul patch control | | | | | 8224 | | | |
| 50 ul patch control | | | | | 8259 | | | |
| 20 ul 2% in 10 ml DMSO on 8/13 tube 21 | | | | | 3321 | | | |
| 20 ul 2% in 10 ml DMSO on 8/13 tube 38 | | | | | 3134 | | | |
| kimwipe control, tube 37 | | | | | 3375 | | | |

Summary and Conclusions of Drug Elution from Patches

The percentage of SADBE lost from the patch, and therefore presumed to be transferred into the skin, was calculated for each patch and the results for a given volume (volume of 2% SADBE solution loaded onto the patch) and time point (time patch was on the pig) were averaged, broken down by whether an elastic bandage held the patch in place on the pig or not, was averaged. The results are shown below in Table 4.

TABLE 4

Average transfer of SADBE into skin by time of exposure, volume loaded on the patch, and whether an elastic bandage was used to hold the patches onto skin. (Note: the percent transferred into skin equals 100% minus the percent detected still in the patch after patch removal. It is assumed that all drug no longer in the patch is transferred into the skin.)

| Time patch worn | With elastic bandage | | | Without elastic bandage | |
|---|---|---|---|---|---|
| | 20 ul | 50 ul | 80 ul | 20 ul | 50 ul |
| 1 hour | 44.3% (n = 2) | 40.6% (n = 2) | 27.4% (n = 2) | | |
| 3 hours | 75.6% (n = 4) | 59.0% (n = 4) | 38.4% (n = 2) | 49.2% (n = 2) | 53.9% (n = 2) |
| 6 hours | 90.9% (n = 4) | 84.1% (n = 4) | 82.3% (n = 2) | 79.5% (n = 2) | 62.6% (n = 2) |
| 24 hours | 95.1% (n = 2) | 97.9% (n = 2) | 97.0% (n = 2) | | |

Conclusions of SADBE Transfer from Patches into Skin

The elastic bandage increased drug absorption into the skin.

At the 1-6 hour time points, larger volumes gave somewhat or slightly less percentage drug transfer. But the percentage of the loaded drug transferred into the skin was more consistent than the absolute volume of drug transferred into the skin. That is, a 4× increase of volume from 20 ul to 80 ul did not result in 4× lower percentage of drug transferred.

By 6 hours, over 80% of the loaded drug was transferred into the skin with all loading volumes tested with the elastic bandage. By 24 hours, over 95% was transferred into the skin.

Skin Irritation

Skin irritation was scored as in in Table 5.

TABLE 5

Scoring System for Skin Reactions

| Reaction | Numerical Grading |
|---|---|
| Erythema (redness) and Eschar (scab) formation | |
| No erythema | 0 |
| Very slight erythema (barely perceptible) | 1 |

TABLE 5-continued

Scoring System for Skin Reactions

| Reaction | Numerical Grading |
|---|---|
| Well-defined (mild) erythema | 2 |
| Moderate erythema | 3 |
| Severe erythema (beet-redness) to eschar formation preventing grading of erythema | 4 |
| Edema (swelling) formation | |
| No edema | 0 |
| Very slight edema (barely perceptible) | 1 |
| Well-defined edema (edges of area well-defined by definite raising) | 2 |
| Moderate edema (raised approximately 1 mm) | 3 |
| Severe edema (raised more than 1 mm and extending beyond exposure area) | 4 |
| Maximum possible score for irritation | 8 |

It was scored 3 times per week at each patch application site for four weeks.

No pigs had edema at any drug application site at any time after patch application and removal. So the scores below are just for erythema.

The erythema scores for each individual patch application are shown in Table 6. The scores shown are the erythema score at the time of patch removal, and then the highest of the 3 scores taken each week for each patch site.

TABLE 6

| Patch number | Pig # | volume on patch | patch removal time hours | net SADBE in skin | Percent of SADBE in skin | score at patch removal | highest score in wk 1 | highest score in wk 2 | highest score in wk 3 |
|---|---|---|---|---|---|---|---|---|---|
| 1 | 1 | 20 ul | 1 | 1452 | 42.8 | | | | |
| 8 | 2 | 20 ul | 1 | 1555 | 45.8 | | | | |

TABLE 6-continued

| Patch number | Pig # | volume on patch | patch removal time hours | net SADBE in skin | Percent of SADBE in skin | score at patch removal | highest score in wk 1 | highest score in wk 2 | highest score in wk 3 |
|---|---|---|---|---|---|---|---|---|---|
| 2 | 1 | 20 ul | 3 | 2658 | 78.3 | | | | 2 |
| 7 | 2 | 20 ul | 3 | 2439 | 71.9 | | | | |
| 25 | 4 | 20 ul | 3 | 2021 | 60.4 | | | | 3 |
| 26 | 4 | 20 ul | 3 | 1272 | 38.0 | | | | |
| 29 | 5 | 20 ul | 3 | 2595 | 77.5 | | 1 | 3 | 3 |
| 30 | 5 | 20 ul | 3 | 2506 | 74.9 | | 1 | 3 | 4 |
| 3 | 1 | 20 ul | 6 | 3128 | 92.2 | | | 3 | 3 |
| 6 | 2 | 20 ul | 6 | 3149 | 92.8 | | | 4 | |
| 27 | 5 | 20 ul | 6 | 3020 | 90.2 | | | 3 | |
| 28 | 5 | 20 ul | 6 | 2958 | 88.4 | | | 3 | 2 |
| 31 | 4 | 20 ul | 6 | 2960 | 88.4 | | | | 3 |
| 32 | 4 | 20 ul | 6 | 2362 | 70.5 | | | | 1 |
| 4 | 1 | 20 ul | 24 | 3211 | 94.6 | | | 4 | 4 |
| 5 | 2 | 20 ul | 24 | 3242 | 95.5 | | | 4 | |
| 9 | 2 | 50 ul | 1 | 3141 | 38.1 | | | 4 | |
| 16 | 1 | 50 ul | 1 | 3551 | 43.0 | | 1 | 3 | 4 |
| 10 | 2 | 50 ul | 3 | 5542 | 67.2 | 1 | 1 | 4 | |
| 15 | 1 | 50 ul | 3 | 6508 | 78.9 | | 1 | 4 | 4 |
| 33 | 4 | 50 ul | 3 | 4184 | 50.8 | 1 | 1 | 3 | 4 |
| 34 | 4 | 50 ul | 3 | 4693 | 56.9 | 1 | 1 | 3 | 4 |
| 37 | 5 | 50 ul | 3 | 4758 | 57.7 | 2 | 3 | 4 | 4 |
| 38 | 5 | 50 ul | 3 | 2643 | 32.1 | | | 3 | 2 |
| 11 | 2 | 50 ul | 6 | 7006 | 84.9 | | 1 | 4 | |
| 14 | 1 | 50 ul | 6 | 7583 | 91.9 | | 2 | 4 | 4 |
| 35 | 5 | 50 ul | 6 | 6293 | 76.4 | | 1 | 3 | 4 |
| 36 | 5 | 50 ul | 6 | 6866 | 83.3 | 2 | 2 | 3 | 3 |
| 39 | 4 | 50 ul | 6 | 5788 | 70.2 | | 1 | 3 | 4 |
| 40 | 4 | 50 ul | 6 | 4525 | 54.9 | | 1 | 1 | 3 |
| 12 | 2 | 50 ul | 24 | 8025 | 97.3 | | 2 | 2 | 4 |
| 13 | 1 | 50 ul | 24 | 8121 | 98.4 | 2 | 2 | 4 | 4 |
| 17 | 3 | 80 ul | 1 | 3246 | 24.6 | 2 | 2 | 1 | |
| 24 | 3 | 80 ul | 1 | 3990 | 30.2 | 2 | 1 | 3 | |
| 18 | 3 | 80 ul | 3 | 3681 | 27.9 | | 2 | 1 | |
| 23 | 3 | 80 ul | 3 | 6464 | 49.0 | 2 | 4 | 4 | |
| 19 | 3 | 80 ul | 6 | 11006 | 83.4 | 2 | 3 | 4 | |
| 22 | 3 | 80 ul | 6 | 10727 | 81.3 | 2 | 2 | 2 | |
| 20 | 3 | 80 ul | 24 | 12689 | 96.1 | 2 | 3 | 4 | |
| 21 | 3 | 80 ul | 24 | 12925 | 97.9 | 2 | 3 | 4 | |

As can be seen generally in Table 6, the erythema scores peaked in week 2 and were down to zero in week 4. This is shown in Table 7, which gives the average score across all patches and doses and exposure times at patch removal, and in weeks 1, 2, and 3 (the average of the highest score for each individual in each of those three weeks). This delayed erythema is characteristic of a delayed-type hypersensitivity response, and SADBE is known to cause a delayed-type hypersensitivity response in humans.

TABLE 7

| Average high erythema score by week. | |
|---|---|
| At patch removal | 0.63 |
| Week 1 | 1.05 |
| Week 2 | 2.60 |
| Week 3 | 1.73 |
| Week 4 | 0.00 |

The erythema scores were higher with larger dose volumes and longer patch wear times, as shown in Table 8. The increase in erythema scores was large from 20 ul to 50 ul, but there was no further increase with the 80 ul dose compared to 50 ul. The increase in erythema scores was dramatic with 3 hours exposure compared to 1 hour, but was less dramatic at 6 and 24 hours compared to 3 hours.

TABLE 8

| Average score weeks 0-3 by dose and exposure time | | | | |
|---|---|---|---|---|
| | 1 hour | 3 hours | 6 hours | 24 hours |
| 20 ul | 0 | 0.83 | 0.92 | 1.5 |
| 50 ul | 1.5 | 2.125 | 1.92 | 2.5 |
| 80 ul | 1.375 | 1.625 | 1.25 | 2.25 |

Summary of Skin Irritation Data

The pigs showed skin irritation that had the characteristics of a delayed-type hypersensitivity response in that erythema increased over time and peaked in the second week, and then resolved by the fourth week. No pig had edema at a patch application site. The erythema was dependent on dose and time of exposure.

Example 5

A Non-Glp Sadbe Dermal Patch Dose Range, Skin Irritation and Toxicity Evaluation in a Guinea Pig Model Purpose/Objective The purpose of this nonGLP study was to evaluate the effect of various concentrations of SADBE delivered via dermal patch, for dose site irritation and toxicity endpoints such as body weights, group food consumption, clinical observation, pre-termination clinical pathology, gross and histopathology.

Test Article(s)

Squaric Acid Dibutylester (SADBE) (2%, 6%, 18%, dermal patch)

Dermal patch (square 4.5×4.5 cm) consists of
Backing layer of 3M Medical Tape 9916 (3M corporation, Saint Paul, MN, USA) (2.2 oz/yd$_2$(62 g/m$_2$) 100% Polyester Tan Spunlace Nonwoven, with a pressure-sensitive acrylate adhesive).
Barrier layer of 3M 9733 polyester film.
Gauze patch of Precision Fabrics PFG 0700-00010 polyester, approximately 3 cm$^2$ area. The gauze patch area is circular with 0.67 inches (1.7 cm) diameter (2.27 cm$^2$ area), with the outer ring sonic welded to the underlying barrier layer, so the more absorbent center portion of the gauze area not sonic welded is 0.55 inches (1.4 cm) in diameter (1.53 cm$^2$ area).
40 lb Paper silicone line (split liner)

Methods

Thirty (30) guinea pigs (15 female and 15 male) were utilized for this nonGLP study. Prior to and post dosing (dermal patches loaded with 20 microliters of 2, 6, or 18% SADBE drug solution) body weights, group food consumption, and Draize scoring for erythema, eschar formation, and edema at the dose site were be recorded. The dermal patch loaded with SADBE was applied to animals, and left in place for ~12 hours plus/minus 1 hour. Following the ~12 hour dosing period, patch sites was assessed by Draize scoring. During this time, animals were observed for signs of toxicity post-dosing, and daily throughout study duration via weekly body weights and daily group food consumption. After the 28 days assessment period, re challenge was performed, a second patch (not treated during the induction phase) was applied and assessed by Draize scoring.

At the end of the survival period, blood was collected for standard hematology and serum chemistry analysis, and the animals humanely euthanized. The second dose site and cervical lymph nodes were collected at necropsy for further histopathological evaluation. Dose site was explanted, fixed, and embedded. Dose sites were examined histologically and an evaluation of cell type presence and tissue response conducted.

Results

The cutaneous application of SADBE via dermal patches to guinea pig skin at any dose tested, had no significant effect on body weight or food consumption.

The first dermal SADBE patch application of 2% SADBE was slightly irritating. The re-challenge with 2% was moderately irritating. The first dermal SADBE patch application of 6% SADBE was moderately irritating. The re-challenge with 6% was moderately irritating. The first dermal SADBE patch application of 18% SADBE was severely irritating. The re-challenge with 18% was moderately irritating.

At all doses, the presence of multifocal rare to mild infiltrates of inflammatory cells composed primarily of lymphocytes, plasma cells and macrophages were observed, accumulated within the dose site. In addition, mild to moderate parakeratosis, minimal multifocal necrosis and fatty infiltration were observed at all SADBE treated sites. Unlike 2-6%, at 18% SADBE minimal multifocal necrosis, moderately thick bands of fibrous connective tissue and multifocal mild neovascularization were observed at the treatment site and this may be a toxic effect. Cervical and Inguinal lymph node sections from both animals in all SADBE treated groups were within normal limits.

Bioanalytical analysis of patches loaded with SADBE indicated the SADBE was stable for more than 12 hours in the patches when not exposed to animal skin with no apparent loss of SADBE or conversion of SADBE to the degradation product, SAMBE. Analysis of patches after the 12 hour exposure on animal skin showed most of the SADBE was lost from the patches and thus presumed to have entered the guinea pig skin.

Cutaneous Irritation and Delayed-Type Hypersensitivity Response

Cutaneous irritation at the test site was observed and scored each day of the study by the Draize Scale for both Erythema & Eschar and Edema. The scale for each is in Tables 9 and 10, each on a 0-4 scale. The cumulative Erythema & Eschar and Edema score was the Primary Irritation Index score, which would therefore be on a 0-8 scale.

TABLE 9

| Draize Scale, Erythema & Eschar Formation Patch Test Reaction Grading Scale | |
| --- | --- |
| No erythema | 0 |
| Very slight erythema (barely perceptible) | 1 |
| Well-defined erythema | 2 |
| Moderate to severe erythema | 3 |
| Severe erythema (beet red) to slight eschar formation (injuries in depth) | 4 |

TABLE 10

| Draize Scale, Edema Formation Patch Test Reaction Grading Scale | |
| --- | --- |
| No edema | 0 |
| Very slight edema (barely perceptible) | 1 |
| Slight edema (edges of area well definited) | 2 |
| Moderate edema (raised approximately 1 mm) | 3 |
| Severe edema (raised more than 1 mm & extracting beyond the area of exposure) | 4 |

To assess the effect of the test article, SADBE (2%, 6%, and 18% in DMSO), on cutaneous skin irritation potential and sensitivity in guinea pig, Draize scoring system was used for dose site evaluation for erythema and eschar responses and for Edema. The test article (20 ul) was loaded on a dermal patch and applied to shaved guinea pig skin for 12 hrs (induction phase). The first dose site evaluation was performed for 30 days post application. A second dose was applied and dose site evaluation was also performed for approximately 5 weeks (challenge phase).

Figure 4:
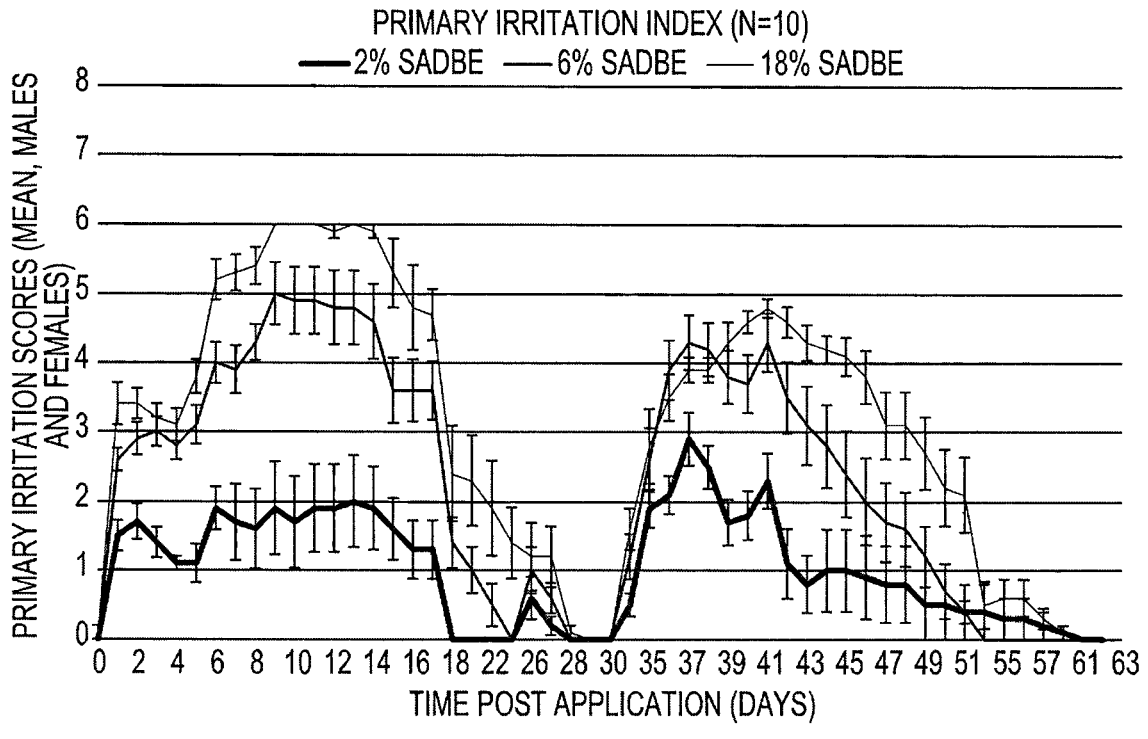
FIG. 4. Primary Irritation Index (pII) daily average for all guinea pigs by dose. Mean±SEM Primary irritation score following SADBE dermal patch application. At induction, animals were dosed with 2%, 6% and 18% SADBE via dermal patch (day 0) and dose site evaluations were performed for the following 30 days. Guinea pig skin was re-challenged and a second SADBE patch (day 34) at the same concentrations was applied at a different location and dose site evaluation was performed for the following 28 days (n=10 per dose level).

The Primary Irritation Index (pII) for each test article dose was calculated to assess the irritation potential. The Primary Irritation Index (pII) is the mean of the primary irritation score. The primary irritation score is the sum of the erythema/eschar score and the edema score, resulting in a maximal irritation potential of 8. The daily primary irritation index (pII) for each test article dose over the course of the study was calculated (FIG. 4). The pII is used to categorize the test article treatments as negligible to not irritating (0-0.9), slight (0.9-1.9), moderate (2-4.9) or severe (5-8) irritation potential. By this scale, 2% SADBE was slightly irritating after the first dose and moderately irritating after the second dose; 6% SADBE was moderately irritating after both doses; and 18% was severely irritating on the first dose and moderately irritating on the second dose. (FIG. 4.)

At induction, during the 28 day observation period, the lowest dose of SADBE tested, 2% SADBE, showed slight cutaneous irritation to shaved guinea pig skin lasting for over ~17 days. When the same guinea pigs were re-challenged with 2% SADBE at a naïve site, the cutaneous irritation reached slight to moderate levels, lasting ~5 days and returned to non-irritating levels ~9 days post-dermal-application.

At induction, during the 28-day observation period, 6% SADBE demonstrated moderate cutaneous irritation lasting for ~18 days, returning to slight irritation and not irritating levels by ~23 days. When the same guinea pigs were re-challenged with 6% SADBE at a naïve site, the cutaneous irritation reached moderate levels, peaked at ~5 days and returned to non-irritating levels ~14 days post-dermal-application.

At induction, during the 28-day observation period, the highest concentration of SADBE tested, 18% SADBE, demonstrated moderate to severe cutaneous irritation of shaved guinea pig skin lasting for ~21 days, returning to slight irritation and not irritating levels by ~27 days post-dosing. When the same Guinea pigs were re-challenged with 18% SADBE at a naïve site, the cutaneous irritation reached moderate levels, peaking at ~8 days, and returned to non-irritating levels ~19 days post-dermal-application.

Animal Health Results

In summary, body weights, food consumption, clinical monitoring and clinical pathology were assessed. Guinea pig body weight was not affected at any time during the study after cutaneous application of the test article and at any of the doses tested. Food consumption was also not affected any time during the study post cutaneous application of the test article. Clinical monitoring observations did not reveal any significant abnormalities.

Histopathology Results

All tissue sample histology slides were examined by the study pathologist using light microscopy.
FemaleTreated Skin Sites (Group 1; 2% SADBE Patch): Five Treatment skin sites were scored. There were multifocal rare to mild infiltrates of inflammatory cells composed primarily of lymphocytes and macrophages in the dermis. Necrosis, neovascularization, fibrosis and fatty infiltration were not noted.

Axillary and Inguinal lymph node sections from all animals were within normal limits. In animal #118037, there was mild multifocal hemorrhage in the corticomedullary region of the mesenteric lymph node that correlates with gross necropsy finding of mottled, dark red discoloration.

MaleTreated Skin Sites (Group 1; 2% SADBE Patch)

Five Treatment skin sites were scored. There were multifocal rare infiltrates of inflammatory cells composed primarily of macrophages in the dermis. Necrosis, neovascularization, fibrosis and fatty infiltration were not noted.

There was mild multifocal hemorrhage in the cortex of the right axillary lymph node of animal #116050 that correlates with gross necropsy finding of dark red discoloration. Axillary and Inguinal lymph node sections from remaining animals were within normal limits.

FemaleTreated Skin Sites (Group 2; 6% SADBE Patch)

Five Treatment skin sites were scored. There were multifocal rare to mild infiltrates of inflammatory cells composed primarily of lymphocytes, plasma cells and macrophages in the dermis. Narrow band of fibrous connective was noted in animal #117356, 117353 and 117367. Necrosis, neovascularization and fatty infiltration were not noted.

There was mild multifocal hemorrhage in the medulla of the right axillary lymph node of animal #117356 that correlates with gross necropsy finding of dark red discoloration. Axillary and Inguinal lymph node sections from remaining animals were within normal limits. In animal #118849, there was mild multifocal hemorrhage in the corticomedullary region of the mesenteric lym node that correlates with gross necropsy finding of mottled, dark red discoloration.

MaleTreated Skin Sites (Group 2; 6% SADBE Patch)

Five Treatment skin sites were scored. There were multifocal rare to mild infiltrates of inflammatory cells composed primarily of plasma cells and macrophages in the dermis. Necrosis, neovascularization, fibrosis and fatty infiltration were not noted.

There was mild multifocal hemorrhage in the cortex of the right inguinal lymph node of animal #116105 that correlates with gross necropsy finding of dark red discoloration. Axillary and Inguinal lymph node sections from remaining animals were within normal limits.

FemaleTreated Skin Sites (Group 3; 18% SADBE Patch)

Five Treatment skin sites were scored. There were multifocal rare to mild infiltrates of inflammatory cells composed primarily of lymphocytes, plasma cells and macrophages in the dermis. Moderately thick bands of fibrous connective was noted in animal #119069. Minimal multifocal necrosis and neovascularization was noted. Fatty infiltration were not noted.

Axillay and Inguinal lymph node sections from all animals were within normal limits.

MaleTreated Skin Sites (Group 3; 18% SADBE Patch)

Five Treatment skin sites were scored. There were multifocal rare to heavy infiltrates of inflammatory cells composed primarily of lymphocytes, plasma cells and macrophages in the dermis. Narrow to moderately thick band of fibrous connective was noted in animal #116102, 116048 and 117906. Minimal, multofocal necrosis and mild multifocal neovascularization was noted. Fatty infiltration were not noted.

There was mild multifocal hemorrhage in the cortex of the right and left axillary lymph nodes of animal #116048 that correlates with gross necropsy finding of dark red discoloration. Axillary and Inguinal lymph node sections from remaining animals were within normal limits.

Bioanalytical Results

American Preclinical Services Study ID STUDY ID: JLM002-PHOO

Introduction

Squaric acid dibutyl ester (SADBE) at 2% (w/v) concentration in dimethylsulfoxide (DMSO) was added to a skin patch for dermal dosing of SADBE to test for a delayed-type hypersensitivity response or other skin irritation. In the laboratories of Squarex HPLC analysis was conducted to analyze for SADBE content, for analysis of the dose formulation prepared by APS and to determine stability of the test article in the dermal patches during the application time and to test for residual SADBE in the dermal patches after 12 hours applied to the animals.

Materials and Methods

The skin patches consisted of a polymer backing layer similar to 3M 9916 polyester nonwoven backing layer with adhesive, 3M 9733 polyester film laminate barrier layer, and Precision Fabrics Group 0700-00010 polyester gauze layer. The gauze was heat sealed to the barrier layer. The gauze patch area was 1.53 cm².

Patches were removed from the pigs at the indicated times and immediately the reservoir portion of the patch was cut out and placed in a 50 ml tube with 10 ml of DMSO.

The tubes of DMSO with patches were transported to the Squarex laboratory, shaken at 200 rpm for 1 hour or more, and then the DMSO from each tube was placed in an injection vial and analyzed for SADBE content by HPLC on a C18 column with the program SADBE3-50 ul. SADBE elutes in this program at about 24.0 minutes and absorbs at 255 nm, so the area of the 24.0 min peak at 255 nm was used to quantify SADBE. The SADBE degradation product squaric acid monobutyl ester (SAMBE) was also quantified by 255 nm area under the curve at the elution time of 12.7 minutes.

The HPLC program details are these:
This program is called SADBE3-50 ul on the HPLC, with 50 ul injection.
Column: USP L1 (ODS), 250 mm×4.6 mm, Sum (C18)
  Agilent part number 880995-902
Mobile phase: A: 25 mM $KH_2PO_4$ (pH5) (not pH adjusted)
  B: Methanol
Flow rate: 1.0 mL/min
Wavelength: 255 nm, 215 nm
Temperature: Room Temperature
Injection volume: 50 ul

TABLE 11

| | Gradient elution: | |
| --- | --- | --- |
| Time (min) | Eluant A (%) | Eluant B (%) |
| 0 | 95 | 5 |
| 5 | 95 | 5 |
| 10 | 50 | 50 |
| 30 | 20 | 80 |
| 30.1 | 95 | 5 |
| 35 | 95 | 5 |

Results

Table 12 shows the test article analysis of the vials prepared by APS. The test article vials of 2%, 6%, and 18% SADBE dissolved in DMSO complied with specifications and had the predicted concentrations of SADBE at 24 hours after preparation.

TABLE 2

| | Test article | |
| --- | --- | --- |
| | % of expected SADBE | SAMBE as percent of SADBE |
| 2% vial | 97.5% | 0.84% |
| 6% vial | 102.9% | 0.83% |
| 18% vial | 97.7% | 0.91% |

Table 13 shows the analysis of patches loaded with 20 ul of 2%, 6%, or 18% SADBE and left gauze side up in air for 12-24 hours. The results indicated the SADBE was stable for more than 12 hours in the patches when not exposed to animal skin. There was no apparent loss of SADBE or conversion of SADBE to SAMBE.

TABLE 13

| | Patch controls after >12 hours in air | |
| --- | --- | --- |
| | % of expected SADBE | SAMBE as percent of SADBE |
| 2% patch | 106.0% | 0.95% |
| 6% patch | 94.5% | 1.05% |
| 18% patch | 100.3% | 1.01% |

Table 14 shows the remaining SADBE and amount of SAMBE degradation product in the patches collected after 12 hours on the guinea pigs, as an average of the 10 patches on 10 animals for each SADBE percentage applied.

TABLE 14

| | 2% patches SADBE as % of expected | SAMBE as % of expected if all SADBE were converted to SAMBE | 6% patches SADBE as % of expected | SAMBE as % of expected if all SADBE were converted to SAMBE | 18% patches SADBE as % of expected | SAMBE as % of expected if all SADBE were converted to SAMBE |
| --- | --- | --- | --- | --- | --- | --- |
| average | 1.32 | 11.72 | 10.67 | 8.87 | 34.13 | 4.33 |
| St. Dev. | 1.26 | 2.28 | 6.11 | 1.08 | 7.21 | 0.68 |
| range | 0.0-1.3 | 7.6-14.7 | 2.7-22.7 | 6.5-10.2 | 23.0-46.5 | 3.6-5.7 |

The results showed with 2% patches less than 2% of the starting SADBE remained in the patches, and only 12% of the lost SADBE was detected as SAMBE degradation product still on the patches. So nearly all of the SADBE was apparently transferred into the guinea pig skin.

With 6% patches, 11% of the SADBE remained on the patch on average, and with the 18% patches, 34% of the SADBE remained on the patch on average. So as the SADBE concentration increased the efficiency of transfer into the skin decreased, but still most of the SADBE was lost from the patch and presumably transferred into skin even with the 18% SADBE patches.

Conclusion

At all doses, no signs of systemic toxicity post-dosing and daily throughout study duration were observed, but some level of dermal toxicity was observed. The lowest concentration of SADBE tested (2%) was slightly irritating after the first dose (with a delay of several days) and was moderately irritating on re-challenge, as scored by primary irritation index (pII) for cutaneous irritation. The highest concentration (18%) tested was severely irritating after the first dose and moderately irritating after re-challenge. At 2-18%, SADBE exhibited dermal irritation potential in guinea pigs and is therefore a cutaneous irritant and cutaneous sensitizer.

Example 6

A Non-GLP SADBE Dermal Patch Dose Range, Skin Irritation and Toxicity Evaluation in a Gottingen Mini-Pig Model

Purpose/Objective

The purpose of this nonGLP study was to evaluate the effect of various concentrations of SADBE delivered via dermal patch, for dose site irritation and toxicity endpoints such as body weights, group food consumption, clinical observation, pre-termination clinical pathology, gross and histopathology.

Test Article(s)

Squaric Acid Dibutylester (SADBE) (2%, 6%, 18% solutions in DMSO, dermal patch)
Dermal patch (square 4.5×4.5 cm) consists of
Backing layer of 3M Medical Tape 9916 (3M corporation, Saint Paul, MN, USA) (2.2 oz/yd$_2$(62 g/m$_2$) 100% Polyester Tan Spunlace Nonwoven, with a pressure-sensitive acrylate adhesive).
Barrier layer of 3M 9733 polyester film.
Gauze patch of Precision Fabrics PFG 0700-00010 polyester, approximately 3 cm$^2$ area. The gauze patch area is circular with 0.67 inches (1.7 cm) diameter (2.27 cm$^2$ area), with the outer ring sonic welded to the underlying barrier layer, so the more absorbent center portion of the gauze area not sonic welded is 0.55 inches (1.4 cm) in diameter (1.53 cm$^2$ area).
40 pound paper silicone liner (split liner)

Methods

A total of 6 Gottingen miniswine (3 female and 3 male) was used in this nonGLP study. Prior to dosing, the baseline body weights, group food consumption, and Draize scoring (see tables 1 and 2) for erythema and eschar formation and edema at the future dose site were recorded. A dermal patch (1 patch/animal) loaded with 20 microliters of 2, 6, or 18% SADBE drug solution was applied to animals, and left in place for ~12 hours. Following the ~12 hour dosing period, patch sites was assessed by Draize scoring as in Example 5, 5x/week for 21 days. During this time, animals were observed for signs of toxicity post-dosing, and daily throughout study duration via weekly body weights and weekly group food consumption. After the 25 day assessment period, the animals were re-challenged and a second dosing and assessment phase performed for 30 days. At the end of the survival period, animals were humanely euthanized and a complete necropsy was performed. The test article vials used to prepare patches and mini-pig exposed patches were collected after application to determine SADBE content and SADBE degradation product squaric acid monobutyl ester (SAMBE) using HPLC at Squarex's Laboratory.

Dose site was explanted, fixed, and embedded. Dose sites were examined histologically and an evaluation of cell type presence and tissue response conducted.

Results

The application of SADBE via dermal patches to min-pig skin at any dose had no significant effect on body weight or food consumption, indicating that the test article did not induce any significant systemic toxicity. Animals did not display any significant signs of toxicity post-dosing and daily throughout study duration.

The first patch application of 2% SADBE applied to mini swine skin via dermal patch was moderately irritating. The re-challenge with 2% was moderately-severely irritating.

The first patch application of 6% SADBE applied to mini swine skin via dermal patch was moderately irritating. The re-challenge with 6% was moderately-severely irritating.

The first patch application of 18% SADBE applied to mini swine skin via dermal patch was moderately-severely irritating. The re-challenge with 18% was severely irritating.

At all doses tested (2-18%) SADBE was moderately irritating on the initial dose and displayed cutaneous irritation in mini-pig skin. The highest concentration of SADBE tested (18%), was severely irritating on re-challenge with a second dose. Thus, SADBE is a cutaneous irritant and sensitizer.

At all doses, multifocal rare to mild infiltrates of inflammatory cells composed primarily of lymphocytes, plasma cells and macrophages were observed in the dermis at the dose site. In addition, mild to moderate parakeratosis, minimal multifocal necrosis and fatty infiltration were observed at all SADBE treated sites. Neovascularization and fibrosis was not noted in any tissue sections examined.

Cervical and Inguinal lymph node sections from both animals in all SADBE treated groups were within normal limits.

Bioanalytical analysis of patches loaded with SADBE indicated the SADBE was stable for more than 12 hours in the patches when not exposed to animal skin with no apparent loss of SADBE or conversion of SADBE to the degradation product SAMBE. The SADBE was lost from the patches applied to mini pigs and thus presumed to have entered the min-pig skin.

Cutaneous Irritation and Delayed-Type Hypersensitivity Response

Cutaneous irritation at the test site was observed and scored each day of the study by the Draize Scale for both Erythema & Eschar and Edema. The scale for each is in Tables 9 and 10 in Example 5, each on a 0-4 scale. The cumulative Erythema & Eschar and Edema score was the Primary Irritation Index score, which would therefore be on a 0-8 scale.

Figure 5:
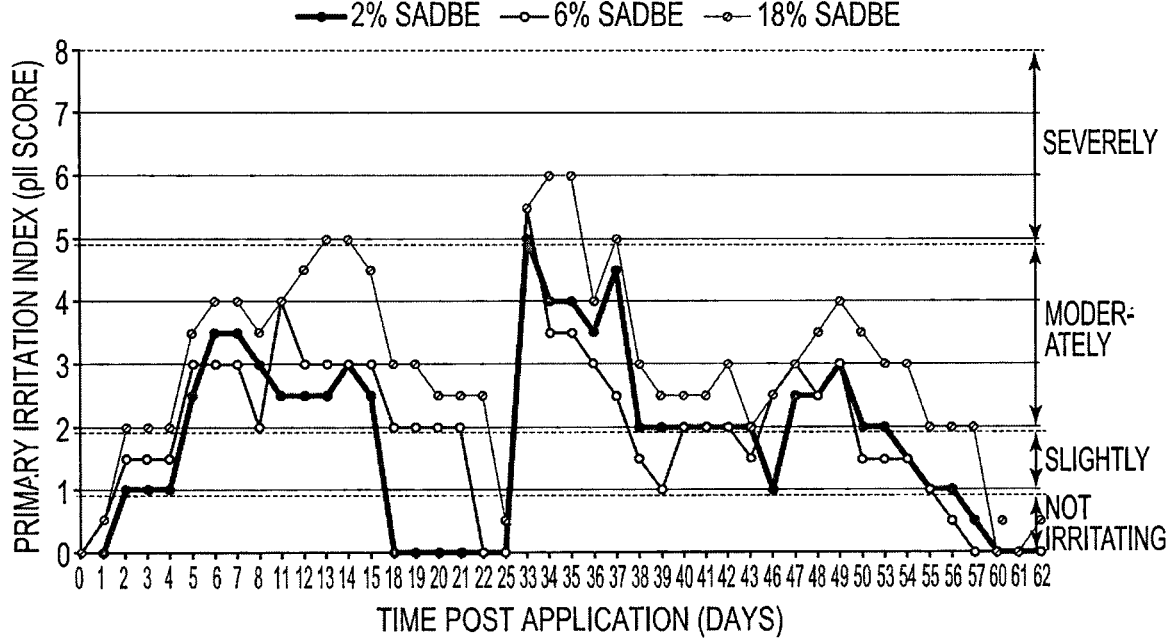
FIG. 5. Primary Irritation Index (pII) daily average for all mini pigs by dose. Mean Primary irritation score following SADBE dermal patch application. At induction, animals were dosed with 2%, 6% and 18% SADBE via dermal patch (day 0) and dose site evaluations were performed for the following 25 days. Mini pig skin was re-challenged and a second SADBE patch (day 32) at the same concentrations was applied at a different location and dose site evaluation was performed for the following 30 days.

The daily primary irritation index (pII) for each test article dose over the course of the study was calculated (FIG. 5). The pII is used to categorize the test article treatments as negligible to not irritating (0-0.9), slight (0.9-1.9), moderate (2-4.9) or severe (5-8) irritation potential. By this scale, 2% SADBE reached moderately irritating levels after the first dose (pII~3.5) and moderately-severely irritating after the second dose (pII transiently peaking at 5); 6% SADBE reached moderately irritating levels after the first dose (pII~3.0-4.0) and was moderately-severely irritating after the second dose (pII transiently peaking at 5.5). SADBE at 18% was moderately-severely irritating on the first dose (pII~5.0) and severely irritating on the second dose (pII~6).

At induction, during the 25 day observation period, the lowest dose of SADBE tested, 2% SADBE, showed moderate cutaneous irritation to shaved mini pig skin lasting for over ~15 days. When the same mini pigs were re-challenged with 2% SADBE at a naïve site, severe cutaneous irritation was observed and this lasted ~1-2 days before going to moderate levels, lasting ~17 days and returning to non-irritating levels ~22 days post-dermal-application.

At induction, during the 28 day observation period, 6% SADBE also showed moderate cutaneous irritation to shaved mini pig skin lasting for ~21 days. When the same mini pigs were re-challenged with 6% SADBE at a naïve site, severe cutaneous irritation was observed and lasted 1 day before going to moderate levels, lasting ~19 days and returned to non-irritating levels ~22 days post-dermal-application.

At induction, during the 28 day observation period, 18% SADBE, the highest concentration tested showed moderate-severe cutaneous irritation to shaved mini pig skin lasting for ~22 days. When the same mini pigs were re-challenged with 18% SADBE at a naïve site, severe cutaneous irritation was observed and this lasted ~5 day before going to moderate levels, lasting ~24 days and returning to non-irritating levels ~26 days post-dermal-application.

Animal Health Results

In summary, body weights, food consumption, clinical monitoring and clinical pathology were assessed. All assessments suggested that animals did not experience any significant toxicity from the application of SADBE.

Gross Necropsy Results

No abnormalities were noted at necropsy.

Histopathology Results

Cervical and Inguinal lymph node sections from all animals were within normal limits.

Test article relative scores were not calculated for the absence of control (untreated) sites.

Tissue sample histology slides (H&E) were examined by the study pathologist using light microscopy. Treated skin sites from animals dosed with 2% & 6% SADBE revealed multifocal rare to mild infiltrates of inflammatory cells composed primarily of lymphocytes, plasma cells and macrophages in the dermis. However, at 18% SADBE, treated skin sites revealed multifocal mild to heavy infiltrates of inflammatory cells composed primarily of lymphocytes, plasma cells and macrophages in the dermis. There was mild to moderate parakeratosis in all sections examined. Cervical and Inguinal lymph node sections from all animals, at all doses were within normal limits.

Analytical Results

American Preclinical Services Study ID STUDY ID: JLM003-PHOO

Introduction

Squaric acid dibutyl ester (SADBE) at 2% (w/v) concentration in dimethylsulfoxide (DMSO) was added to a skin patch for dermal dosing of SADBE to test for a delayed-type hypersensitivity response or other skin irritation. In the laboratories of Squarex HPLC analysis was conducted to analyze for SADBE content, for analysis of the dose formulation prepared by APS and to determine stability of the test article in the dermal patches during the application time and to test for residual SADBE in the dermal patches after 12 hours applied to the animals.

Materials and Methods

The skin patches consisted of a polymer backing layer similar to 3M 9916 polyester nonwoven backing layer with adhesive, 3M 9733 polyester film laminate barrier layer, and Precision Fabrics Group 0700-00010 polyester gauze layer. The gauze was heat sealed to the barrier layer. The gauze patch area was 1.53 $cm^2$.

Patches were removed from the pigs at the indicated times and immediately the reservoir portion of the patch was cut out and placed in a 50 ml tube with 10 ml of DMSO.

The tubes of DMSO with patches were transported to the Squarex laboratory, shaken at 200 rpm for 30 minutes to overnight, and then the DMSO from each tube was placed in an injection vial and analyzed for SADBE content by HPLC on a C18 column with the program SADBE3-50 ul. SADBE elutes in this program at about 24.0 minutes and absorbs at 255 nm, so the area of the 24.0 min peak at 255 nm was used to quantify SADBE. The SADBE degradation product squaric acid monobutyl ester (SAMBE) was also quantified by 255 nm area under the curve at the elution time of 12.7 minutes.

The HPLC program details are these:

This program is called SADBE3-50 ul on the HPLC, with 50 ul injection.

Column: USP L1 (ODS), 250 mm×4.6 mm, 5 um (C18)
    Agilent part number 880995-902
Mobile phase: A: 25 mM $KH_2PO_4$ (pH5) (not pH adjusted)
    B: Methanol
Flow rate: 1.0 mL/min
Wavelength: 255 nm, 215 nm
Temperature: Room Temperature
Injection volume: 50 ul

TABLE 15

| Gradient elution: | | |
| --- | --- | --- |
| Time (min) | Eluant A (%) | Eluant B (%) |
| 0 | 95 | 5 |
| 5 | 95 | 5 |
| 10 | 50 | 50 |
| 30 | 20 | 80 |
| 30.1 | 95 | 5 |
| 35 | 95 | 5 |

Results

Table 16 shows the test article analysis of the vials prepared by APS. The test article vials of 2%, 6%, and 18% SADBE dissolved in DMSO complied with specifications and had the predicted concentrations of SADBE at 24 hours after preparation.

TABLE 16

| Test article | | |
| --- | --- | --- |
| | % of expected SADBE | SAMBE as percent of SADBE |
| 2% vial | 100.8% | 0.88% |
| 6% vial | 97.5% | 0.96% |
| 18% vial | 104.4% | 1.00% |

Table 17 shows the analysis of patches loaded with 20 ul of 2% or 6% SADBE and left gauze side up in air for 12-24 hours. The results indicated the SADBE was stable for more than 12 hours in the patches when not exposed to animal skin. There was no apparent loss of SADBE or conversion of SADBE to SAMBE.

TABLE 17

| Patch controls after >12 hours in air | | |
| --- | --- | --- |
| | % of expected SADBE | SAMBE as percent of SADBE |
| 2% patch | 97.7% | 0.86% |
| 6% patch | 96.8% | 0.96% |
| 18% patch | not done | |

Table 18 shows the remaining SADBE and amount of SAMBE degradation product in the patches collected after 12 hours on the mini-pigs.

| | 2% patches | | 6% patches | | 18% patches | |
| --- | --- | --- | --- | --- | --- | --- |
| Animal # | SADBE as % of expected | SAMBE as % of expected if all SADBE were converted to SAMBE | SADBE as % of expected | SAMBE as % of expected if all SADBE were converted to SAMBE | SADBE as % of expected | SAMBE as % of expected if all SADBE were converted to SAMBE |
| 1st animal | 7.0 | 0.80 | 29.9 | 4.38 | 65.2 | 1.20 |
| 2nd animal | 14.6 | 0.91 | 40.8 | 4.00 | 65.8 | 1.73 |
| average | 10.8 | 0.86 | 35.4 | 4.19 | 65.5 | 1.47 |

The results showed with 2% patches about 11% of the starting SADBE remained in the patches, and less than 1% of the starting SADBE was detected as SAMBE degradation product still on the patches. So about 89% of the SADBE was apparently transferred into the mini pig skin.

Increasing percentages of the starting SADBE amount remained on the patches with 6% and 18% patches. With 6% patches, 35% of the starting SADBE remained on the patch; and with 18% patches, 65% of the starting SADBE remained on the patch. Thus, a majority of the SADBE left the patch in the 6% patches, and about ⅓ left the patch in the 18% patches, but still an increasing absolute amount of SADBE was lost from the patches and thus presumed to have entered the skin with increasing concentration of SADBE loaded on the patches, although the increasing amount lost and presumed transferred into the skin was less than proportional to the concentration loaded on the patch.

Conclusion

At all doses, no signs of systemic toxicity post-dosing and daily throughout study duration were observed, but dermal toxicity was observed.

All concentrations of SADBE tested (2-18%) were moderately irritating after the first dose (with a delay of several days) and were moderately-severely irritating on re-challenge, as scored by primary irritation index (pII) for cutaneous irritation. The highest concentration (18%) tested was moderately irritating after the first dose and severely irritating after re-challenge. At 2-18%, SADBE exhibited dermal irritation potential in mini pigs and is therefore a cutaneous irritant and cutaneous sensitizer.

Example 7

Kit with Dermal Patch and Glass Swab Filled with DMSO

We purchased from James Alexander Corp. (Blairstown, NJ, USA) 0.6 ml glass swabs filled with 0.6 ml of DMSO. The glass swabs were as in FIG. 2 with a sealed glass ampoule (45 mm length, 5 mm inner diameter), a polyolefin flat-topped swab (10 mm height), wrapped in a cellolose acetate butyrate barrier layer, and with a removable cardboard sleeve.

We purchased two designs of custom manufactured dermal patches from Innovize Corp. (Vadnais Heights, MN, USA). The dermal patches were as in FIG. 1 with these elements:

Dermal patch (square 4.5×4.5 cm) consists of

Backing layer of 3M Medical Tape 9916 (3M corporation, Saint Paul, MN, USA) (2.2 oz/yd$_2$(62 g/m$_2$) 100% Polyester Tan Spunlace Nonwoven, with a pressure-sensitive acrylate adhesive).

Barrier layer of 3M 9733 polyester film.

Gauze patch of Precision Fabrics PFG 0700-00000 polyester, approximately 3 cm$^2$ area. The gauze patch area is circular with 0.67 inches (1.7 cm) diameter (2.27 cm$^2$ area), with the outer ring sonic welded to the underlying barrier layer, so the more absorbent center portion of the gauze area not sonic welded is 0.55 inches (1.4 cm) in diameter (1.53 cm$^2$ area).

40 pound paper silicone liner (split liner)

Option 2 of dermal patches was the same except with gauze consisting of Precision Fabrics Group PFG 0700-00010.

The inventor crushed the vial, by hand then tipped and squeezed gently once, then let gravity work. In less than a minute the foam tip was wet and it could start wetting the patch when the tip was dabbed or wiped onto the gauze of the dermal patch. The inventor dabbed the foam tip onto the gauze until it was visibly wet over about 90% of its area. The patch was weighed immediately before adding DMSO and immediately after adding DMSO to get a net weight of DMSO applied.

Gauze 0700-00010. 38.6 mg to get 90% wetted (10% or so dry spots still). 41.4 mg to get 100% wetted. 52 mg to get as wet as much as possible with dabbing.

Second run with a separate 0700-00010 patch. 41.6 mg to completely wet. 48.7 mg to get as wet as possible with dabbing. Add a drop, and the weight was now 85 mg. The drop was absorbed; it did not drip off.

Patches with 0700-00000 fabric. 34.4 mg to completely wet. (That is 100% visibly wet, comparable to the 41.4 and 41.6 mg measurements with the 0700-00010 patches.) 35.2 mg with further wetting (this is comparable to the 52 and 48.7 mg measurements with the 0700-00010 patches). If you add a drop, it runs off the gauze. If you wipe that with a kimwipe, the mass is 43.5 mg left on the patch.

Second run with a separate 0.700-00000 patch, 31 mg to get 100% visibly wetted by dabbing.

The new 00000 material had sharper wetted borders than the 00010 material, so it was easier to see the area that was wet. The 00010 material wicked more, which is probably why the borders did not seem as sharp and clear. The 00010 gauze could absorb a full drop, but the 00000 gauze could not without dripping off when the patch was put in a vertical orientation.

REFERENCES

Palli M A, McTavish H, Kimball A, Horn T D. Immuno-therapy of Recurrent Herpes Labialis With Squaric Acid. *JAMA Dermatol.* 2017; 153:828-829.

McTavish H, Zerebiec K W, Zeller J C, Shekels L L, Matson M A, Kren B T. Immune characteristics correlating with HSV-1 immune control and effect of squaric acid dibutyl ester on immune characteristics of subjects with frequent herpes labialis episodes. *Immun. Inflamm. Dis.* 2019; 7(1):22-40.

Chang A L S, Honari G, Guan L, Zhao L, Palli M A, Horn T D, Dudek A Z, McTavish H. A phase 2, multi-center, placebo-controlled study of single dose squaric acid dibutyl ester (SADBE) to reduce frequency of out-breaks in subjects with recurrent herpes labialis. *J Am Acad Dermatol.* 2020 Apr. 11:S0190-9622(20)30561-2. doi: 10.1016/j.jaad.2020.04.021.

Buckley D A, Du Vivier A W P. The therapeutic use of topical contact sensitizers in benign dermatoses. *British Journal of Dermatology* 2001; 145: 385-405.

Lee A N, Mallory S B. Contact immunotherapy with squaric acid dibutylester for the treatment of recalci-trant warts. *J Am Acad Dermatol* 1999; 41:595-599.

All references cited are hereby incorporated by reference.

What is claimed is:

1. A method of applying a topical immunosensitizer, the method comprising:
obtaining a kit comprising:
(a) dermal patch comprising:
an adhesive backing layer comprising a fabric over-laid by an adhesive over at least part of the area of the fabric; the adhesive backing layer overlaid over a portion of its area by
an absorbent gauze layer; and
(b) a sealed container containing a liquid solution, the solution comprising a topical immunosensitizer dis-solved in a vehicle; and
(c) an absorbent swab;
opening the sealed container;
dipping the absorbent swab in the liquid solution in the container to wet the swab;
contacting the wet swab with the absorbent gauze layer of the dermal patch to wet the absorbent gauze layer and produce a loaded dermal patch loaded with the liquid solution; and
applying the loaded dermal patch to the skin of a human.

2. The method of claim 1 wherein the step of dipping the absorbent swab in the liquid solution absorbs more than half of the volume of the liquid solution in the container.

3. The method of claim 1 wherein the step of contacting the wet swab with the absorbent gauze layer visibly wets 80 to 100% of the area of the absorbent gauze layer.

4. The method of claim 1 wherein
the solution is a liquid solution and the vehicle comprises dimethylsulfoxide (DMSO), acetone, isopropanol, butanol, isobutanol, or ethanol.

5. The method of claim 4 wherein the vehicle comprises DMSO.

6. The method of claim 4 wherein the topical immuno-sensitizer is a squaric acid ester.

7. The method of claim 6 wherein the topical immuno-sensitizer is squaric acid dibutylester (SADBE), and the liquid solution comprises less than 50 ppm water.

8. The method of claim 1 wherein the vehicle is DMSO and the topical immunosensitizer is SADBE.

9. A method of topically applying a controlled dose of a topical immunosensitizer comprising:
applying and adhering to skin of a human an adhesive dermal patch comprising:
a backing layer comprising a fabric overlaid by an adhesive over at least part of the area of the fabric; the backing layer overlaid over a portion of its area by
an absorbent gauze layer;
the absorbent gauze layer comprising a liquid or semi-liquid solution comprising a vehicle and a topical immunosensitizer dissolved in the vehicle.

10. The method of claim 9 further comprising before the applying step:
opening a unit dose container containing a liquid or semi-liquid solution comprising a vehicle and a topical immunosensitizer dissolved in the vehicle, and
applying the solution to the absorbent gauze layer of the dermal patch to form the absorbent gauze layer com-prising the liquid or semi-liquid solution comprising the vehicle and the topical immunosensitizer dissolved in the vehicle.

11. The method of claim 10 wherein after the opening step the method comprises dipping an absorbent swab in the liquid or semi-liquid solution to wet the absorbent swab; and the step of applying the solution to the absorbent gauze layer comprises contacting the wetted absorbent swab with the gauze layer to visibly wet the gauze over 80% to 100% of the area of the absorbent gauze layer.

12. The method of claim 11 wherein the solution is a liquid solution and the step of dipping the absorbent swab in the liquid solution absorbs more than half of the volume of the liquid solution in the container onto the absorbent swab.

13. The method of claim 9 wherein the vehicle is DMSO and the topical immunosensitizer is SADBE.

* * * * *